(12) United States Patent
Clausen et al.

(10) Patent No.: US 6,995,004 B2
(45) Date of Patent: Feb. 7, 2006

(54) UDP-N-ACETYLGLUCOSAMINE: GALACTOSE-β 1,3-N-ACETYLGALACTOSAMINE-α-R / N-ACETYLGLUCOSAMINE-β 1,3,-N-ACETYLGALACTOSAMINE-α-R (GLCNAC TO GALNAC) β1,6-N-ACETYLGLUCOSAMINYLTRANSFERASE, C2/4GNT

(75) Inventors: Henrik Clausen, Holte (DK); Tilo Schwientek, Brønshøj (DK)

(73) Assignee: Glycozym ApS, Holte (DK)

( * ) Notice: Subject to any disclaimer, the term of this patent is extended or adjusted under 35 U.S.C. 154(b) by 242 days.

(21) Appl. No.: 09/874,390

(22) Filed: Jun. 4, 2001

(65) Prior Publication Data

US 2002/0081656 A1 Jun. 27, 2002

Related U.S. Application Data

(63) Continuation of application No. PCT/DK99/00677, filed on Dec. 3, 1999.

(30) Foreign Application Priority Data

Dec. 4, 1998 (DK) .................................. PA 1998 01605

(51) Int. Cl.
*C12P 21/06* (2006.01)
*C12N 9/00* (2006.01)
*C12N 9/10* (2006.01)
*C12N 1/20* (2006.01)
*C07H 21/04* (2006.01)

(52) U.S. Cl. .................. 435/193; 435/4; 435/6; 435/15; 435/69.1; 435/183; 435/193; 435/252.3; 435/320.1; 435/16; 435/17; 435/18; 530/350; 536/23.2; 536/23.3; 536/23.4; 536/23.5; 536/23.6; 536/23.7

(58) Field of Classification Search ............ 435/4, 435/6, 15–18, 69.1, 183, 193, 252.3, 320.1, 435/325, 255.1, 348, 363; 530/350; 536/23.2–23.7
See application file for complete search history.

(56) References Cited

U.S. PATENT DOCUMENTS 5,766,910 A  6/1998  Fukuda et al.
6,136,580 A  10/2000  Fukuda et al.

FOREIGN PATENT DOCUMENTS

EP  0 590 747 A2  4/1994

(Continued)

OTHER PUBLICATIONS

Adams et al. GenBank Accession No. AA315469, Apr. 19, 1997.*

(Continued)

*Primary Examiner*—Manjunath N. Rao
(74) *Attorney, Agent, or Firm*—Darby & Darby

(57) ABSTRACT

A novel gene defining a novel human UDP-GlcNAc: Gal/GlcNAcβ 1-3GalNAc αβ1, 6GlcNAc-transferase, termed C2/4GnT, with unique enzymatic properties is disclosed. The enzymatic activity of C2/4GnT is shown to be distinct from that of previously identified enzymes of this gene family. The invention discloses isolated DNA molecules and DNA constructs encoding C2/4GnT and derivatives thereof by way of amino acid deletion, substitution or insertion exhibiting C2/4GnT activity, as well as cloning and expression vectors including such DNA, cells transfected with the vectors, and recombinant methods for providing C2/4GnT. The enzyme C2/4GnT and C2/4GnT-active derivatives thereof are disclosed, in particular soluble derivatives comprising the catalytically active domain of C2/4GnT. Further, the invention discloses methods of obtaining 1,6-N-acetyl glucosaminyl glycosylated saccharides, glycopeptides or glycoproteins by use of an enzymically active C2/4GnT protein or fusion protein thereof or by using cells stably transfected with a vector including DNA encoding an enzymatically active C2/4GnT protein as an expression system for recombinant production of such glycopeptides or glycoproteins. Also a method for the identification for the identification of DNA sequence variations in the C2/4GnT gene by isolating DNA from a patient, amplifying C2/4GnT-coding exons by PCR, and detecting the presence of DNA sequence variation are disclosed.

24 Claims, 9 Drawing Sheets

FOREIGN PATENT DOCUMENTS

| | | |
|---|---|---|
| WO | WO 94/07917 | 7/1994 |
| WO | WO 95/07020 | 3/1995 |

OTHER PUBLICATIONS

NCI–CGAP, GenBank Accession No. AA583339, Sep. 8, 1997.*

Ropp P.A., et al. Mucin Biosynthesis: Purification and Characterization of a Mucin β6N–Acetylglucosaminyltransferase. *The Journal of Biological Chemistry*, (1991) Vol. 286, No. 35, Issue of Dec. 15, pp. 23863–23871.

Schwientek, et al., *Control of O–glycan branch formation. Molecular cloning of human cDNA encoding a novel .beta. 1,6–N–acetylglucosaminyltransferase forming core 2 and 4.*, Abstract, 10.04.00.

Yeh, Jiunn–Chern, et al., *Molecular cloning and expression of a novel .beta.–1,6–N–acetylglucosaminyltransferase that forms core 2, core 4, and I branches.*, Abstract, 10.04.00.

Gcg Geneseq D:V59800, Abstract (sequences), Jan. 19, 1999.

Clausen, H., et al., *A family of UDP–GalNAc: polypeptide N–acetylgalactosaminyl–transferase control the initiation of muncin–type O–linked glycosylation.*, Glycobiology vol. 6 No. 6 pp. 635–646, 1996.

Piller, F., et al., *Human T–lympocyte Activation Is Associated with Changes in O–glycan Biosynthesis*, The Journal of Biological Chemistry, 1988 by The American Society for Biochemistry and Molecular Biology, Inc. vol. 263, No. 29, Issue Oct. 15, pp: 15146–15150, 1988.

Yang, Ji–Mao, et al.,*Alterations of O–glycan biosynthesis in human colon cancer tissues*, Glycobiology vol. 4 No. 6 pp. 873–884, 1994.

Fukuda, Minoru, *Possible Roles of Tumor–associated Carbohydrate Antigens*, Cancer Reaserch 56, 2237–2244, May 15, 1996.

Brockenhausen, Inka, et al., *Mechanisms underlying aberrant glycosation of MUCl mucin in breast cancer cells*, Eur. J. Biochem. 223, 607–617, 1995.

Brockenhausen, Inka, et al., *Biosynthesis of O–Glycans in Luekocytes from Normal Donors and from Patients with Leukemia: Increase in O–Glycan Core 2 UPD–GlcNAc:Galβ3GaIN Acα–R (GIcNAc to GaINAc) β(1–6)–N–Acetylglucosaminyl transferase in Leukemic Cells.*, Cancer Research 51, 1257–1263, Feb. 15, 1991.

Higgins, Elizabeth A., *Aberrant O–Linked Oligosaccharide Biosynthesis in Lymphocytes and Platelets fron Patients with the Wiskott–Aldrich Syndrome.* The Journal of Biological Chemistry, vol. 266 No. 10, Issue of Apr. 5, pp. 6280–6290, 1991.

Saitoh, Osamu, et al., T–Lymphocytic Leukemia Express Complex, Branched O–Linked Oligosaccharides on a Major Sialoglycoprotein, Leukosialin, Blood, vol. 77 No. 7, Apr. 1, 1991: pp. 1491–1499.

Springer, Georg F., *T and Tn, General Carcinoma Antigens*, Science, vol. 224: pp. 1198–1206.

Kumar, R., et al., *Core2 β–1,6–N–Acetylglucosaminyltransferase Enzyme Activity is Critical for P–Selectin Glycoprotein Ligand–1 Binding to P–Selectin*, Blood, vol. 88, No. 10, Nov. 15, 1996: pp. 3872–3879.

Bierhuizen, Marti F.A., et al., *Expression cloning of a cDNA encoding UPD–GIcN Ac:Gal β1–3–GaINAc–R GIcNAc to GaINAc) β1–6GIcN Ac Transferase by gene transfer into CHO cells expressing polyoma large tumor antigen*, Proc. Natl. Acad. Sci. USA., vol. 89, pp. 9326–9330, Oct. 1992.

Bierhuizen, Marti F.A., et al., *Genomic organization of core and I branching β–1,6–N–Acetylglucosaminyl–transferase. Implication for evolution of the β–1,6–N–acetylaminyltransferase gene family*, Glycobiology, vol. 5 No. 4: pp. 417–425, 1995.

Almedia, Raquel, et al., *A Family of Human β4–Galactosyltransferase*, The Journal Of Biological Chemistry, vol. 272, No. 51, Issue of Dec. 19, pp. 31979–31991, 1997.

Bennett, Eric Paul, et al., *cDNA Cloning and Expression of a Novel Human UPD–N–Acetyl–α–D–galactosamine.*The Journal Of Biological Chemistry, vol. 271, No. 29, Issue of Jul. 19, pp. 17006–17012, 1996.

Wandall, Hans H., et al., *Substrate Specificities of Three Members of the Human UDP–N–Acetyl–β–D–galactoseamine: Polypeptide N–Acetylgalactosaminyltransferase Family, GaINAc–T1,–T2, and –T3*, The Journal of Biological Chemistry, vol. 272, No. 38, issue of Sep. 19, pp. 23503–23514, 1997.

Sutherlin, Marie E., et al., *Expression of Three UDP–N–acetyl–α–D–galactosamine: Polypeptide GaIcNAc N–Acetylgalactosaminyltransferases in Adenocarcinoma Cell Lines*, Cancer Research 57, 4744–4784, Nov. 1, 1997.

Almeida et al., Glycoconjugate J. 1997, 14:S44.

Asano, M. et al. EMBO J. 16:1850–1857, 1997.

Axford, J.S. et al., Autoimmunity 17:157–163, 1994.

Breathnach, R. et al.., Ann. Rev. Biochem. 50:349–83, 1981.

Brew, K. et al., Biochemistry 59:491–97, 1968.

D'Agostaro, G. et al., Eur. J. Biochem. 183:211–217, 1989.

Devereux et al., Nucleic Acids Research, 1984; 12(1).

Fujita–Yamaguchi, Y. et al., J. Biol. Chem. 256:(6):2701–2706, Mar. 25, 1981.

Furukawa, K. et al., Inter. Immunology 2(1):105–112, 1990.

Gentzsch, M. and Tanner, W. (1996) EMBO J., 15:5752–5759.

Hollis, G.F. et al., Biophys Res Comm. 162:1069–1075, 1989.

Johnston, D. et al. (1998) J. Biol. Chem. 273(4):1888–1895.

Keusch, J., et al., Glycobiology 5:365–700, 1995.

Kobata, A. Eur J. Biochem. 209:483–501,1992.

Kozak, M., Ann Rev Cell Biol. 8:197–225, 1992.

Lo et al., Glycobiology (1998), 8:517–526.

Lu, Q., et al.,Develop Biol. 18:257–267, 1997.

Malissard, M., et al., (1996) Eur J. Biochem. 239:340–348.

Masri, K.A., et al., (1988) Biochem Res Comm. 157:657–663.

Matteucci et al., J. Am. Chem. Soc., 1981; 103:3185–3191.

Mengle–Gaw, L., et al. (1985) Biophys Res Comm. 176:1269–1276.

Moscarello M.A., et al. (1991) Biochim Biophys Acta. 831:192–200.

Nakazawa, K. et al. (1988) J. Biochem. 104:165–168.

Nakazawa K. et al. (1991) Eur J. Biochem. 196:363–368.

Narimatsu, H. et al. (1986) Proc Natl Acad Sci USA. 83:4720–4724.

Parquet, M.R. et al., (1984) Biochem J. 218:745–751.

Perillo et al., J. Mol. Med., 1998; 76:402–412.

Perillo et al., Nature, 1995; 378:736–739.

Piller et al., Journ. of Biol. Chem., 1988; 263(29):15146–15150.

Powell, J.T. and Brew, K. (1974) Eur J Biochem. 48:217–228.

Sato, T. et al., (1988) Biochem & Biophysical Res. Comm. 244(3):637–641.

Shaper, J.H. et al. (1995) Glycoconjugate J. 12:477.

Shaper, N.L. et al. (1986) Proc Nat'l Acad Sci USA. 83:1573–1577.
Shaper, N.L. et al. (1988) J. Biol. Chem. 263:10420–10428.
Shaper, N.L. et al. (1997) J. Biol. Chem. 272:31389–31399.
Sheares, B.T. and Carlson, D. (1984) J. Biol. Chem. 259:8045–8047.
Shur, B.D. (1982) J. Biol. Chem. 257:6871–6878.
Williams et al., Journ. of Biol. Chem., 1980; 255(23):11247–11252.
Wilson, I.B. et al. (1993) J. Rheumatol. 20:1282–1287.
Yang et al., Glycobiology, 1994; 4(6):873–884.
Yeh et al., Journ. of Biol. Chem., 1999; 274(5):3215–3221.
Yoo et al., Journ. of Biol. Chem., 1989; 264(29):17078–17083.
U.S. Appl. No. 60/425,204.
U.S. Appl. No. 10/292,896.
U.S. Appl. No. 09/118,464.
U.S. Appl. No. 10/132,652.
U.S. Appl. No. 09/645,192.
U.S. Appl. No. 10/084,406.

* cited by examiner

```
C2/4GnT : MVQWKRICQLHYLWALGCYMLLATVALKLSFRLKCDSDHEGLESRESQSYCRNILYNFLKLPAKRSINGSGVTRGFQEAVLQAI : 85
C2GnT   : --MLRTLRRRLFSYPTKYFEMVLVLSLITFSV-----IRIHQKP---EFVSVRHLELAGENPSSDINCTKVLQGLVNEIQKVK : 74
IGnT    : ----------MPLSMRYLFIISVSSVIIGIV----------------FSVFNEGDESFQRLNISDPLR---------LTQVC : 48

C2/4GnT : LNNLEVKKREP-FIDTHYLSLTRCEHFKAERKEIQFPLSKEEVFPIAYSMVFHEKIENERLFRAVYAPQNIYCVHVDEKSP : 169
C2GnT   : LEILTVKFKKREFIPDDYLNMLSDCSSFIKRRKYIVEPLSKEEAEFPIAYSIVFHIKHEMLDRLIRAIYMPONEYCVHVDTKSE : 159
IGnT    : TSFING---KTRFLMKNKLMIHEKSSCKEYLTQSHYITAPLSKEEADFPLAYIMVIHHHFDTEARLFRAIYMPONIYCVHVDEKAT : 131

C2/4GnT : ETEREAVKAIISCFPNMFIASKLVRVVYASVISRVQADLNCMEDLLQSSVPMKYFLNLHCGTDFFRKSNAEMVCALKMLNGRNSMES : 254
C2GnT   : DSYLAAVMGIASCFSNVFVASRLESVVFIASVISRVQADLNCMKDIYFMSANMKYLINLCGMDFPIKNLEIVRKLRLIMGENNLET : 244
IGnT    : TEERKDAVEQLLSCFPNAFLASKMEPVVYGGISRLQADLNCIRDLSAFEVSMKYVINTACGQDFPLKINKEILVQYLKGFKGKNITPG : 216

C2/4GnT : EVFKHKETRYKY-HFEWVRDTLH----LTNKKKDEPPYNMHMETGNAYIVASRDEVQHVLKNRRSCQLIEMVKDTYSPDEHWAT : 335
C2GnT   : ERMPSHKEERMKK-RYEVVNGKLT---NTGTVRKMLPPLETPLESGSSAYFVVSRFYVGYVIQNEKIQKLMEWAQDTYSPDEYLWAT : 325
IGnT    : VLEPAHAIGRTKYVHQEHLGKELSYVIRTTALKPEPEHNLLTIYEGSAYVALSREFANFVLHDPRAVDLLQWSKDTFSPDEHFWVL : 301

C2/4GnT : LQRARWMPGSVPNHPKYFISDMTSIARLVKWQGHEGGIDKGAPYAPCSGIHQRALCVVGAGDLNMMIQNHILLANKFDPKVEDNA : 420
C2GnT   : IQRIPEVPGSLPASHKYDLSDMQAVARFVKMCYFEGDVSKGAPYPPCDGVHVRSVCIEGAGDLMLRKHILEANKFDVDLFA : 410
IGnT    : LNRLEGVPGSMPN------ASWIGNLRAIKMSDME-DRHGG------CHGHYVHGICLYKGNGDIKVLVNSPSLFANKELNTYPLT : 374

C2/4GnT : LQCLEEYURYKAIYGTEL------------------------ : 438
C2GnT   : IQCLDEHRHKALETLKH------------------------- : 428
IGnT    : VECLELRHRERTLNQSETAIQPSWYF---------------- : 400
```

B | PANC-1 | Capan-1 | Capan-2 | AsPC-1 | BxPC-3 | COLO 357 | HT-29 kb 4.7 –

1.9 –

28S –

C2/4GnT

TSHC78: 5'-GCTCGGTCTCCACCTGTCTCC-3'

TSHC79: 5'-CCACAGGTAGCAACGCTCTCA-3'

UDP-N-ACETYLGLUCOSAMINE: GALACTOSE-β 1,3-N-ACETYLGALACTOSAMINE-α-R / N-ACETYLGLUCOSAMINE-β 1,3,-N-ACETYLGALACTOSAMINE-α-R (GLCNAC TO GALNAC) β1,6-N-ACETYLGLUCOSAMINYLTRANSFERASE, C2/4GNT

This is a continuation of international application Ser. No. International Application Ser. No. PCT/DK99/00677, filed Dec. 3, 1999, the entire disclosure of which is hereby incorporated by reference.

TECHNICAL FIELD

The present invention relates generally to the biosynthesis of glycans found as free oligosaccharides or covalently bound to proteins and glycolipids. This invention is more particularly related to a family of nucleic acids encoding UDP-N-acetylglucosamine: N-acetylgalactosamine β1,6-N-acetylglucosaminyltransferases (Core-β1,6-N-acetylglucosaminyltransferases), which add N-acetylglucosamine to the hydroxy group at C6 of 2-acetamido-2-deoxy-D-galactosamine (GalNAc) in O-glycans of the core 3 and the core 1 type. This invention is more particularly related to a gene encoding the third member of the family of O-glycan , β1,6-N-acetylglucosaminyltransferases, termed C2/4GnT, probes to the DNA encoding C2/4GnT, DNA constructs comprising DNA encoding C2/4GnT, recombinant plasmids and recombinant methods for producing C2/4GnT, recombinant methods for stably transforming or transfecting cells for expression of C2/4GnT, and methods for identification of DNA polymorphism in patients.

BACKGROUND OF THE INVENTION

O-linked protein glycosylation involves an initiation stage in which a family of N-acetylgalactosaminyltransferases catalyzes the addition of N-acetylgalactosamine to serine or threonine residues (1). Further assembly of O-glycan chains involves several sucessive or alternative biosynthetic reactions: i) formation of simple mucin-type core 1 structures by UDP-Gal: GalNAcα-R β1,3Gal-transferase activity; ii) conversion of core 1 to complex-type core 2 structures by UDP-GlcNAc: Galβ1-3GalNAcα-R β1,6GlcNAc-transferase activities; iii) direct formation of complex mucin-type core 3 by UDP-GlcNAc: GlcNAcα β1,3GlcNAc-transferase activities; and iv) conversion of core 3 to core 4 by UDP-GlcNAc: GlcNAcβ1-3GalNAcα-R β1,6GlcNAc-transferase activity. The formation of 1,6GlcNAc branches (reactions ii and iv) may be considered a key controlling event of O-linked protein glycosylation leading to structures produced upon differentiation and malignant transformation (2–6). For example, increased formation of GlcNAcβ1-6GalNAc branching in O-glycans has been demonstrated during T-cell activation, during the development of leukemia, and for immunodeficiencies like Wiskott-Aldrich syndrome and AIDS (7; 8). Core 2 branching may play a role in tumor progression and metastasis (9). In contrast, many carcinomas show changes from complex O-glycans found in normal cell types to immaturely processed simple mucin-type O-glycans such as T (Thomsen-Friedenreich antigen; Gal 1-3GalNAc 1-R), Tn (GalNAc 1-R), and sialosyl-Tn (NeuAc 2-6GalNAc 1-R) (10). The molecular basis for this has been extensively studied in breast cancer, where it was shown that specific downregulation of core 2 β6GlcNAc-transferase was responsible for the observed lack of complex type O-glycans on the mucin MUCl (6). O-glycan core assembly may therefore be controlled by inverse changes in the expression level of Core-β1,6-N-acetylglucosaminyltransferases and the sialyltransferases forming sialyl-T and sialyl-Tn.

Interestingly, the metastatic potential of tumors has been correlated with increased expression of core 2 β6GlcNAc-transferase activity (5). The increase in core 2 β6GlcNAc-transferase activity was associated with increased levels of poly N-acetyllactosamine chains carrying sialyl-Le$^x$, which may contribute to tumor metastasis by altering selectin mediated adhesion (4; 11). The control of O-glycan core assembly is regulated by the expression of key enzyme activities outlined in FIG. 1; however, epigenetic factors including posttranslational modification, topology, or competition for substrates may also play a role in this process (11).

The in vitro biosynthesis of a subset of complex O-glycopeptide structures is presently hampered by lack of availability of the enzymes adding N-acetylglucosamine in a β1-3 linkage to GalNAcα1-O-Ser/Thr to form core 3 as well as the enzyme catalyzing the successive addition of β1-6 N-acetylglucosamine branches to form core 4. This structure is required for the enzymes responsible for further build-up of core 4 based complex type O-glycans (FIG. 1). Most other enzymes required for elongation of branched O-glycans are available, and the core 2/4 enzyme described herein now makes the synthesis of core 4 based structures possible.

Access to the gene encoding C2/4GnT would allow production of a glycosyltransferase for use in formation of core 2 or core 4—based O-glycan modifications on oligosaccharides, glycoproteins and glycosphingolipids. This enzyme could be used, for example in pharmaceutical or other commercial applications that require synthetic addition of core 2 or core 4 based O-glycans to these or other substrates, in order to produce appropriately glycosylated glycoconjugates having particular enzymatic, immunogenic, or other biological and/or physical properties.

Consequently, there exists a need in the art for UDP-N-Acetylglucosamine: Galactose-β1,3-N-Acetylgalactosamine-α-R/N-Acetylglucosamine-β1,3-N-Acetyl-galactosamine-α-R (GlcNAc to GalNAc) β1-6 N-Acetylglucosaminyltransferase and the primary structure of the gene encoding these enzyme. The present invention meets this need, and further presents other related advantages.

SUMMARY OF THE INVENTION

The present invention provides isolated nucleic acids encoding human UDP-N-acetylglucosamine: N-acetylgalactosamine β1,6 N-acetylglucosaminyltransferasee (C2/4GnT), including cDNA and genomic DNA C2/4GnT has broader acceptor substrate specificities compared to C2GnT, as exemplified by its activity with core 3—R saccharide derivatives. The complete nucleotide sequence of C2/4GnT is set forth in SEQ ID NO:1 and FIG. 2.

In one aspect, the invention encompasses isolated nucleic acids comprising the nucleotide sequence of nucleotides 496–1812 as set forth in SEQ ID NO:1 and FIG. 2 or sequence-conservative or function-conservative variants thereof Also provided are isolated nucleic acids hybridizable with nucleic acids having the sequence as set forth in SEQ ID NO:1 and FIG. 2 or fragments thereof or sequence-conservative or function-conservative variants thereof, preferably, the nucleic acids are hybridizable with C2/4GnT sequences under conditions of intermediate stringency, and, most preferably, under conditions of high stringency. In one embodiment, the DNA sequence encodes the amino acid sequence shown in SEQ ID NO:2 and FIG. 2 from methionine (amino acid no. 1) to leucine (amino acid no. 438). In another embodiment, the DNA sequence encodes an amino acid sequence comprising a sequence from phenylalanine (no. 31) to leucine (no. 438) of the amino acid sequence set forth in SEQ ID NO:2 and FIG. 2.

In a related aspect, the invention provides nucleic acid vectors comprising C2/4GnT DNA sequences, including but not limited to those vectors in which the C2/4GnT DNA sequence is operably linked to a transcriptional regulatory element, with or without a polyadenylation sequence. Cells comprising these vectors are also provided, including without limitation transiently and stably expressing cells. Viruses, including bacteriophages, comprising C2/4GnT-derived DNA sequences are also provided. The invention also encompasses methods for producing C2/4GnT polypeptides. Cell-based methods include without limitation those comprising: introducing into a host cell an isolated DNA molecule encoding C2/4GnT, or a DNA construct comprising a DNA sequence encoding C2/4GnT; growing the host cell under conditions suitable for C2/4GnT expression; and isolating C2/4GnT produced by the host cell. A method for generating a host cell with de novo stable expression of C2/4GnT comprises: introducing into a host cell an isolated DNA molecule encoding C2/4GnT or an enzymatically active fragment thereof (such as, for example, a polypeptide comprising amino acids 31–438 of the amino acid sequence set forth in SEQ ID NO:2 and FIG. 2), or a DNA construct comprising a DNA sequence encoding C2/4GnT or an enzymatically active fragment thereof; selecting and growing host cells in an appropriate medium; and identifying stably transfected cells expressing C2/4GnT. The stably transfected cells may be used for the production of C2/4GnT enzyme for use as a catalyst and for recombinant production of peptides or proteins with appropriate galactosylation. For example, eukaryotic cells, whether normal or diseased cells, having their glycosylation pattern modified by stable transfection as above, or components of such cells, may be used to deliver specific glycoforms of glycopeptides and glycoproteins, such as, for example, as immunogens for vaccination.

In yet another aspect, the invention provides isolated C2/4GnT polypeptides, including without limitation polypeptides having the sequence set forth in SEQ ID NO:2 and FIG. 2, polypeptides having the sequence of amino acids 31–438 as set forth in SEQ ID NO:2 and FIG. 2, and a fusion polypeptide consisting of at least amino acids 31–438 as set forth in SEQ ID NO:2 and FIG. 2 fused in frame to a second sequence, which may be any sequence that is compatible with retention of C2/4GnT enzymatic activity in the fusion polypeptide. Suitable second sequences include without limitation those comprising an affinity ligand or a reactive group.

In another aspect of the present invention, methods are disclosed for screening for mutations in the coding region (exon III) of the C2/4GnT gene using genomic DNA isolated from, e.g., blood cells of patients. In one embodiment, the method comprises: isolation of DNA from a patient; PCR amplification of coding exon III; DNA sequencing of amplified exon DNA fragments and establishing therefrom potential structural defects of the C2/4GnT gene associated with disease.

These and other aspects of the present invention will become evident upon reference to the following detailed description and drawings.

BRIEF DESCRIPTION OF THE DRAWINGS

FIG. 2 depicts the DNA sequence of the C2/4GnT (SEQ ID NO:1; accession # AF038650) gene and the predicted amino acid sequence of C2/4GnT. (SEQ ID NO:2). The amino acid sequence is shown in single letter code. The hydrophobic segment representing the putative transmembrane domain is double under-lined. Two consensus motifs for N-glycosylation are indicated by asterisks. The location of the primers used for preparation of the expression constructs are indicated by single underlining. A potential polyadenylation signal is indicated in boldface underlined type.

FIG. 3 is an illustration of a sequence comparison between human C2GnT (SEQ ID NO:11); (accession # M97347), human C2/4GnT (SEQ ID NO:2; accession # AF038650), and human I-GnT (SEQ ID NO: 12; accession # Z19550). Introduced gaps are shown as hyphens, and aligned identical residues are boxed (black for all sequences, and grey for two sequences). The putative transmembrane domains are underlined with a single line. The positions of conserved cysteines are indicated by asterisks. One conserved N-glycosylation sites is indicated by an open circle.

DETAILED DESCRIPTION OF THE INVENTION

Figure 1:
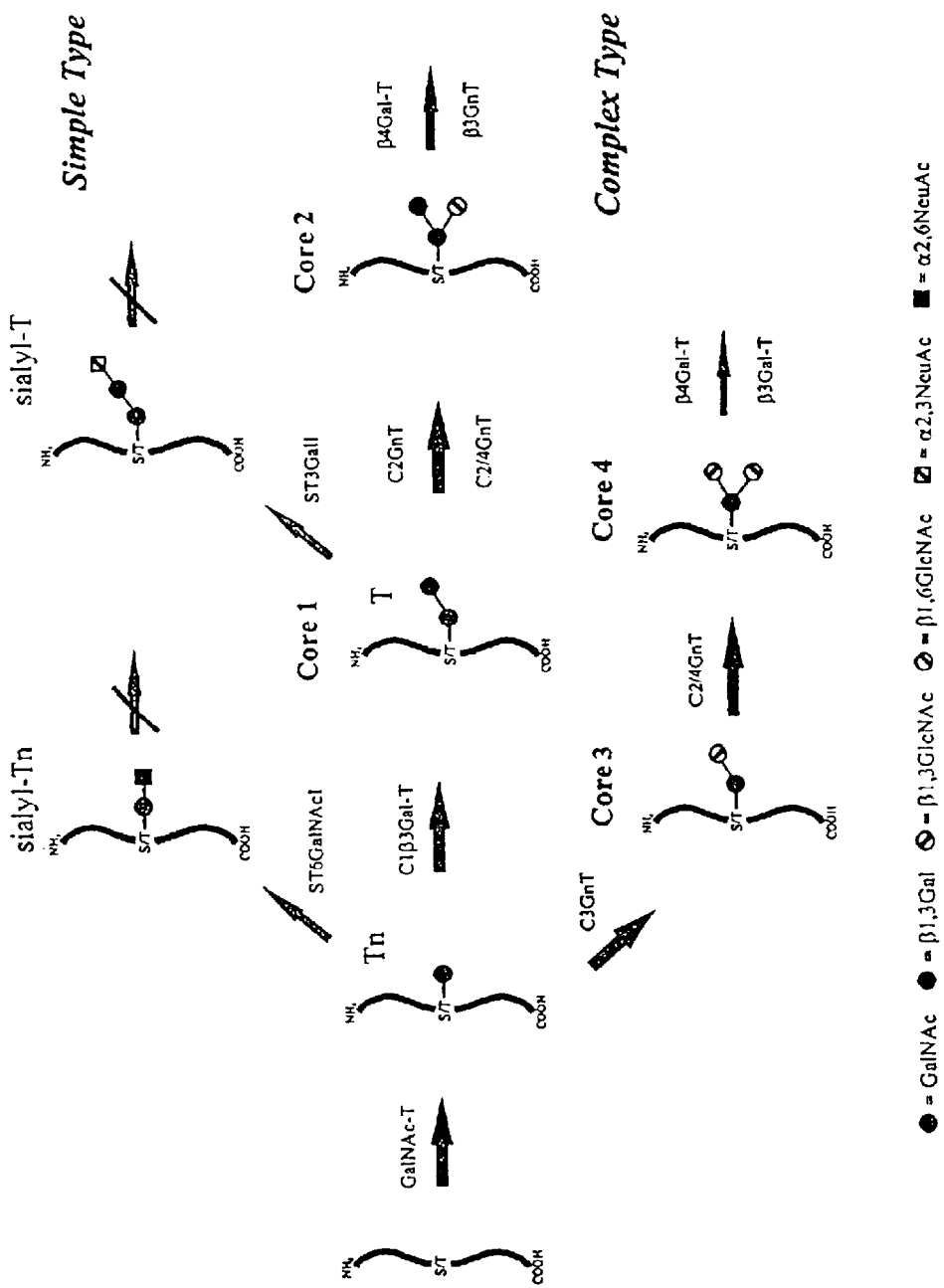
FIG. 1 depicts the biosynthetic pathways of mucin-type O-glycan core structures. The abbreviations used are GalNAc-T: polypeptide αGalNAc-transferase; ST6GalNAcI: mucin α2,6 sialyltransferase; C1β3Gal-T: core 1 β1,3 galactosyltransferase; C2GnT: core 2 β1,6 GlcNAc-transferase; C2/4GnT: core2/core 4 β1,6 GlcNAc-transferase; C3GnT: core 3 β1,3 GlcNAc-transferase; ST3GalI: mucin α2,3 sialyltransferase; β4Gal-T: β1,4 galactosyltransferase; β3Gal-T: β1,3 galactosyltransferase; β3GnT: elongation β1,3 GlcNAc-transferase.

All patent applications, patents, and literature references cited in this specification are hereby incorporated by reference in their entirety. In the case of conflict, the present description, including definitions, is intended to control.

Definitions:

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases (see below).

2. "Complementary DNA or cDNA" as used herein refers to a DNA molecule or sequence that has been enzymatically synthesized from the sequences present in a mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA which has no introns is inserted adjacent to, or within, exogenous DNA sequences.

3. A plasmid or, more generally, a vector, is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule.

4. Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15 M NaCl, 0.015 M Na citrate.)

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A "probe" refers to a nucleic acid that forms a hybrid structure with a sequence in a target region due to complementarity of at least one sequence in the probe with a sequence in the target region.

7. A nucleic acid that is "derived from" a designated sequence refers to a nucleic acid sequence that corresponds to a region of the designated sequence. This encompasses sequences that are homologous or complementary to the sequence, as well as "sequence-conservative variants" and "function-conservative variants". Sequence-conservative variants are those in which a change of one or more nucleotides in a given codon position results in no alteration in the amino acid encoded at that position. Function-conservative variants of C2/4GnT are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties (such as, for example, acidic, basic, hydrophobic, and the like).

8. A "donor substrate" is a molecule recognized by, e.g., a Core-β1,6-N-acetyl-glucosaminyltransferase and that contributes an N-acetylglucosaminyl moiety for the transferase reaction. For C2/4GnT, a donor substrate is UDP-N-acetylglucosamine. An "acceptor substrate" is a molecule, preferably a saccharide or oligosaccharide, that is recognized by, e.g., an N-acetylglucosaminyltransferase and that is the target for the modification catalyzed by the transferase, i.e., receives the N-acetylglucosaminyl moiety. For C2/4GnT, acceptor substrates include without limitation oligosaccharides, glycoproteins, O-linked core 1- and core 3-glycopeptides, and glycosphingolipids comprising the sequences Gal 1-3GalNAc, GlcNAc 1-3GalNAc or Glc 1-3GalNAc.

The present invention provides the isolated DNA molecules, including genomic DNA and cDNA, encoding the UDP-N-acetylglucosamine: N-acetylgalactosamine 1,6 N-acetylglucosaminyltransferases (C2/4GnT).

C2/4GnT was identified by analysis of EST database sequence information, and cloned based on EST and 5'RACE cDNA clones. The cloning strategy may be briefly summarized as follows: 1) synthesis of oligonucleotides derived from EST sequence information, designated TSHC27 (SEQ ID NO:3) and TSHC28 (SEQ ID No.4); 2) successive 5'-rapid amplification of cDNA ends (5'RACE) using commercial Marathon-Ready cDNA; 3) cloning and sequencing of 5'RACE cDNA; 4) identification of a novel cDNA sequence corresponding to C2/4GnT; 5) construction of expression constructs by reverse-transcription-polymerase chain reaction (RT-PCR) using Colo205 human cell line mRNA; 6) expression of the cDNA encoding C2/4GnT in Sf9 (*Spodoptera frugiperda*) cells. More specifically, the isolation of a representative DNA molecule encoding a novel second member of the mammalian UDP-N-acetylglucosamine: β-N-acetylgalactosamine β1,6-N-acetylglucosaminyltransferase family involved the following procedures described below.

Identification of DNA Homologous C2nT.

Database searches were performed with the coding sequence of the human C2GnT sequence (12) using the BLASTn and tBLASTn algorithms against the dbEST database at The National Center for Biotechnology Information, USA. The BLASTn algorithm was used to identify ESTs representing the query gene (identities of 95%), whereas tBLASTn was used to identify non-identical, but similar EST sequences. ESTs with 50–90% nucleotide sequence identity were regarded as different from the query sequence. One EST with several apparent short sequence motifs and cysteine residues arranged with similar spacing was selected for further sequence analysis.

Cloning of Human C2/4GnT.

EST clone 178656 (5' EST GenBank accession number AA307800), derived from a putative homologue to C2GnT, was obtained from the American Type Culture Collection, USA. Sequencing of this clone revealed a partial open reading frame with significant sequence similarity to C2GnT. The coding region of human C2GnT and a bovine homologue was previously found to be organized in one exon ((13), and unpublished observations). Since the 5' and 3' sequence available from the C2/4GnT EST was incomplete but likely to be located in a single exon, the missing 5' and 3' portions of the open reading frame was obtained by sequencing genomic P1 clones. P1 clones were obtained from a human foreskin genomic P1 library (DuPont Merck Pharmaceutical Co. Human Foreskin Fibroblast P1 Library) by screening with the primer pair TSHC27 (5'-GGAAGTTCATACAGTTCCCAC-3') (SEQ ID NO:3) and TSHC28 (5'-CCTCCCATTCAACATCTTGAG -3') (SEQ ID NO:4). Two genomic clones for C2/4GnT, DPMC-HFF#1-1026(E2) and DPMC-HFF#1-1091(F1) were obtained from Genome Systems Inc. DNA from P1 phage was prepared as recommended by Genome Systems Inc. The entire coding sequence of the C2/4GnT gene was represented in both clones and sequenced in full using automated sequencing (ABI377, Perkin-Elmer). Confirmatory sequencing was performed on a cDNA clone obtained by PCR (30 cycles at 95° C. for 15 sec; 55° C. for 20 sec and 68° C. for 2 min 30 sec) on total cDNA from the human COLO 205 cancer cell line with the sense primer TSHC54 (5'- GCAGAATTCATGGTTCAATGGAAGAGACTC-3') (SEQ ID NO:7) and the anti-sense primer TSHC45 (5'-AGCGAATTCAGCTCAAAGTTCAGTCCCATAG -3') (SEQ ID NO:5). The composite sequence contained an open reading frame of 1314 base pairs encoding a putative protein of 438 amino acids with type II domain structure predicted by the TMpred-algorithm at the Swiss Institute for Experimental Cancer Research (ISREC) (http://www isrec.isb-sib.chfsoftware/TMPRED_form.html). The sequence of the 5'-end of C2/4GnT mRNA including the translational start site and 5'-UTR was obtained by 5' rapid amplification of cDNA ends (35 cycles at 94° C. for 20 sec; 52° C. for 15 sec and 72° C. for 2 min) using total cDNA from the human COLO 205 cancer cell line with the anti-sense primer TSHC48 (5'-GTGGGAACTGTATGAACTTCC-3') (SEQ ID NO:6) (FIG. 2).

Expression of C2/4GnT.

Figure 2:
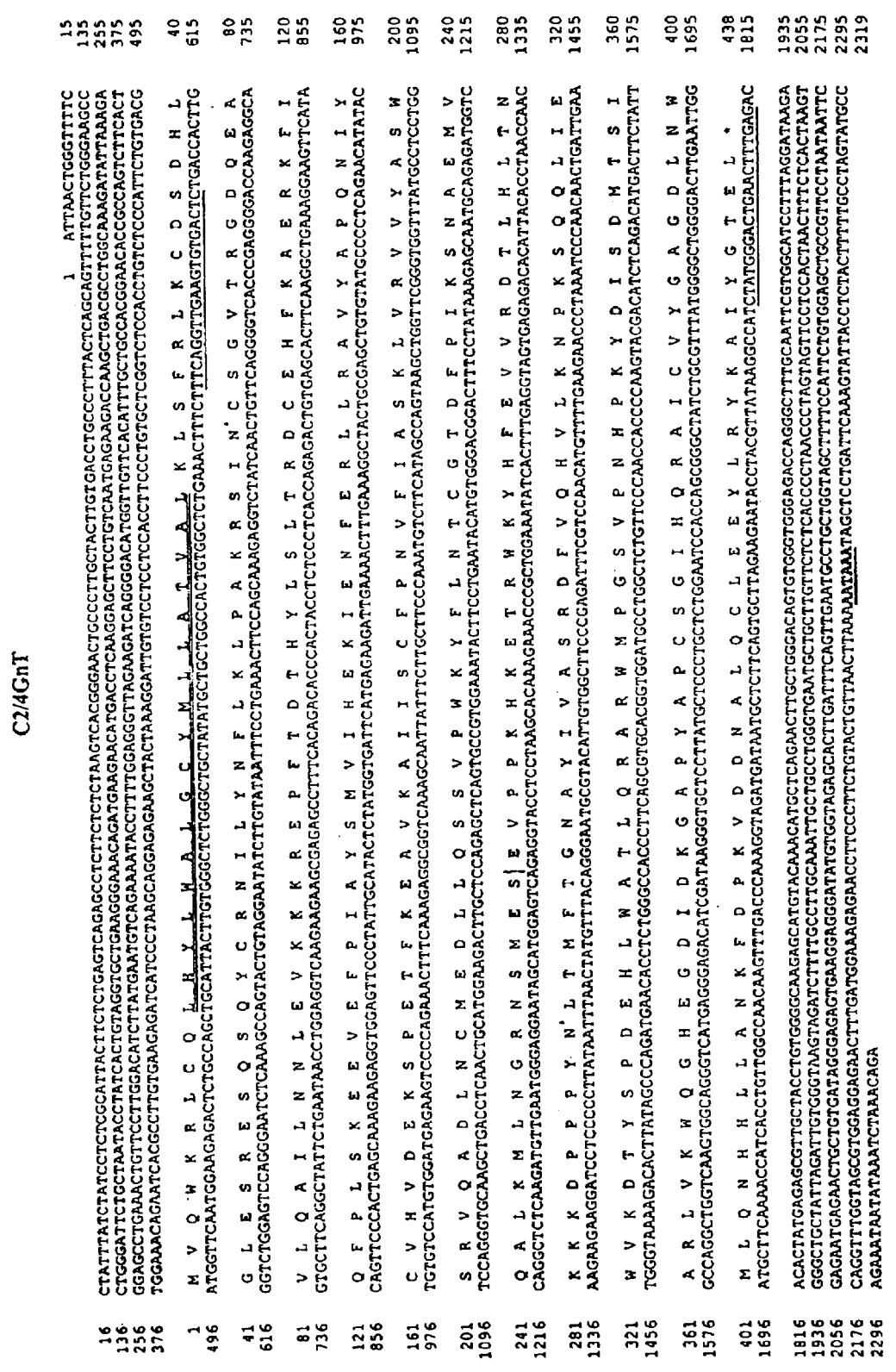

An expression construct designed to encode amino acid residues 31–438 of C2/4GnT was prepared by PCR using P1 DNA, and the primer pair TSHC55 (5'-CGAGAATTCAGGTTGAAGTGTGACTC-3') (SEQ ID NO:8) and TSHC45 (SEQ ID NO:5) (FIG. 2). The PCR product was cloned into the EcoRI site of pAcGP67A (PharMingen), and the insert was fully sequenced. pAcGP67-C2/4GnT-sol was co-transfected with Baculo-Gold™ DNA (PharMingen) as described previously (14). Recombinant Baculo-virus were obtained after two successive amplifications in Sf9 cells grown in serum-containing medium, and titers of virus were estimated by titration in 24-well plates with monitoring of enzyme activities. Transfection of Sf9-cells with pAcGP67-C2/4GnT-sol resulted in marked increase in GlcNAc-transferase activity compared to uninfected cells or cells infected with a control construct. C2/4GnT showed significant activity with disaccharide derivatives of O-linked core 1 (Galβ1-3GalNAcα1-R) and core 3 structures (GlcNAcβ1-3GalNAcα1-R). In contrast, no activity was found with lacto-N-neotetraose as well as GlcNAcβ1-3Gal-Me as acceptor substrates indicating that C2/4GnT has no IGnT-activity. Additionally, no activity could be detected wih α-D-GalNAc-1- para-nitrophenyl indicating that C2/4GnT does not form core 6 (GlcNAcβ1-6GalNAcα1-R) (Table I). No substrate inhibition of enzyme activity was found at high acceptor concentrations up to 20 mM core1—para-nitrophenyl or core3—para-nitrophenyl. C2/4GnT shows strict donor substrate specificity for UDP-GlcNAc, no activity could be detected with UDP-Gal or UDP-GalNAc (data not shown).

TABLE I

Substrate specificities of C2/4GnT and C2GnT

| Substrate | C2/4GnT[a] | | C2Gnt | |
|---|---|---|---|---|
| | 2 mM nmol/h/mg | 10 mM nmol/h/mg | 2 mM nmol/h/mg | 10 mM nmol/h/mg |
| β-D-Gal-(1-3)-α-D-GalNAc | 2.8 | 7.3 | 9.6 | 19.0 |
| β-D-Gal-(1-3)-α-D-GalNAc-1-p-Nph | 16.1 | 21.8 | 16.2 | 23.6 |
| β-D-GlcNAc-(1-3)-α-D-GalNAc-1-p-Nph | 5.2 | 7.4 | <0.1 | <0.1 |
| α-D-GalNAc-1-p-Nph | <0.1 | <0.1 | <0.1 | <0.1 |
| D-GalNAc | <0.1 | <0.1 | <0.1 | <0.1 |
| lacto-N-neo-tetraose | <0.1 | <0.1 | <0.1 | <0.1 |
| β-D-GlcNAc-(1-3)-β-D-Gal-1-Mc | <0.1 | <0.1 | <0.1 | <0.1 |

[a]Enzyme sources were partially purified media of infected High Five ™ cells (see "Experimental Procedures"). Background values obtained with uninfected cells or cells infected with an irrelevant construct were subtracted.
[b]Me, methyl; Nph, nitrophenyl.

Controls included the pAcGP67-GalNAc-T3-sol (15). The kinetic properties were determined with partially purified enzymes expressed in High Five™ cells. Partial purification was performed by consecutive chromatography on Amberlite IRA-95, DEAE-Sephacryl and CM-Sepharose essentially as described (16).

Northern Blot Analysis of Human Organs.

Figure 4A:
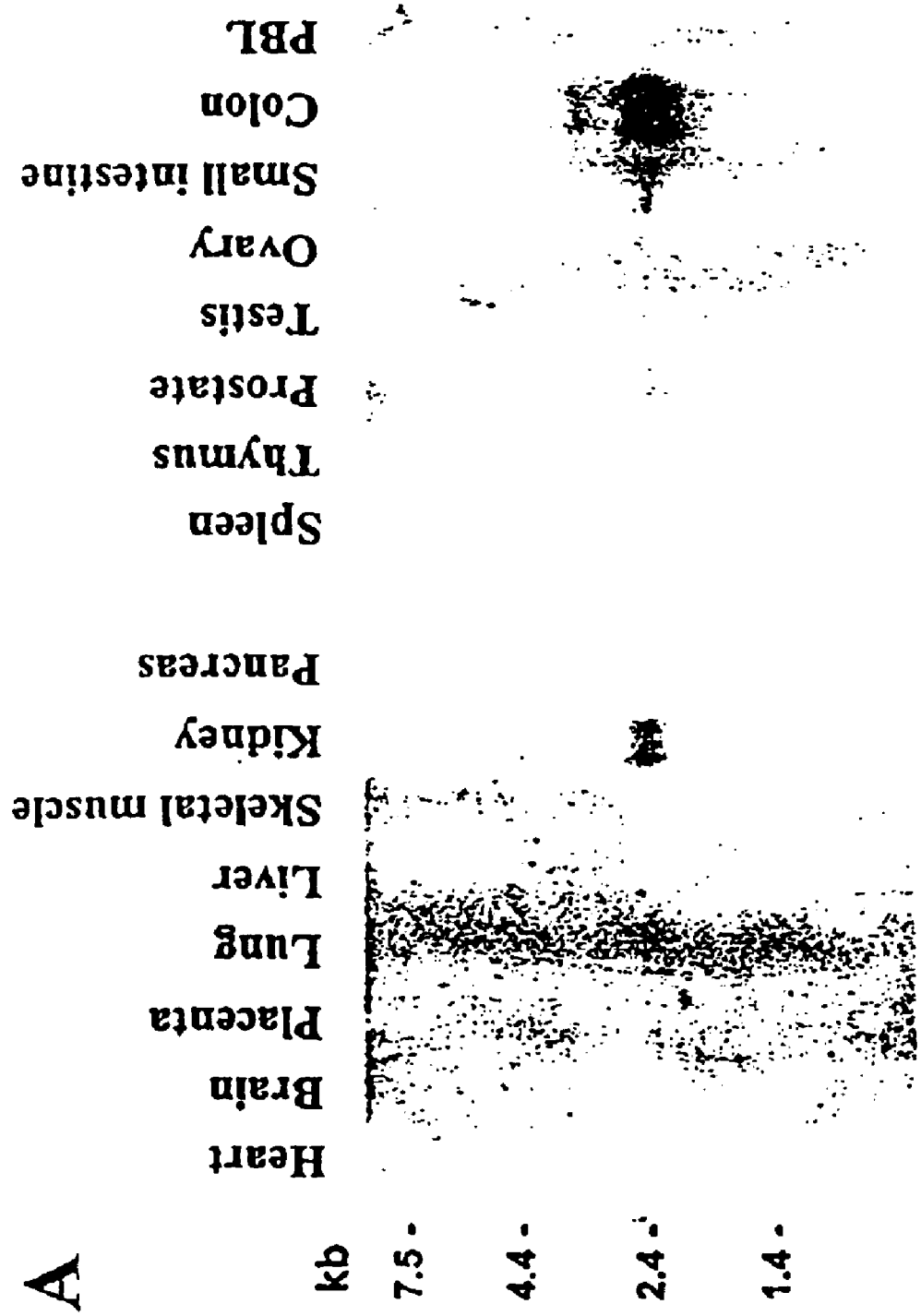
FIG. 4 depicts a Northern blot analysis of healthy human tissues and gastric cancer cell lines. Panel A: Multiple human tissue northern blots, MTN I and MTN II, from Clontech were probed with a $^{32}$P-labeled probe corresponding to the soluble expression fragment of C2/4GnT (base pairs 91–1317). Panel B: A northern blot of total RNA from human colonic and pancreatic cancer cell lines was probed as described for panel A.
Figure 4B:
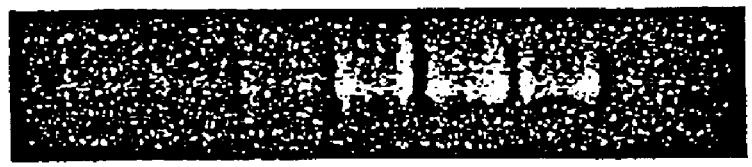
Figure 5:
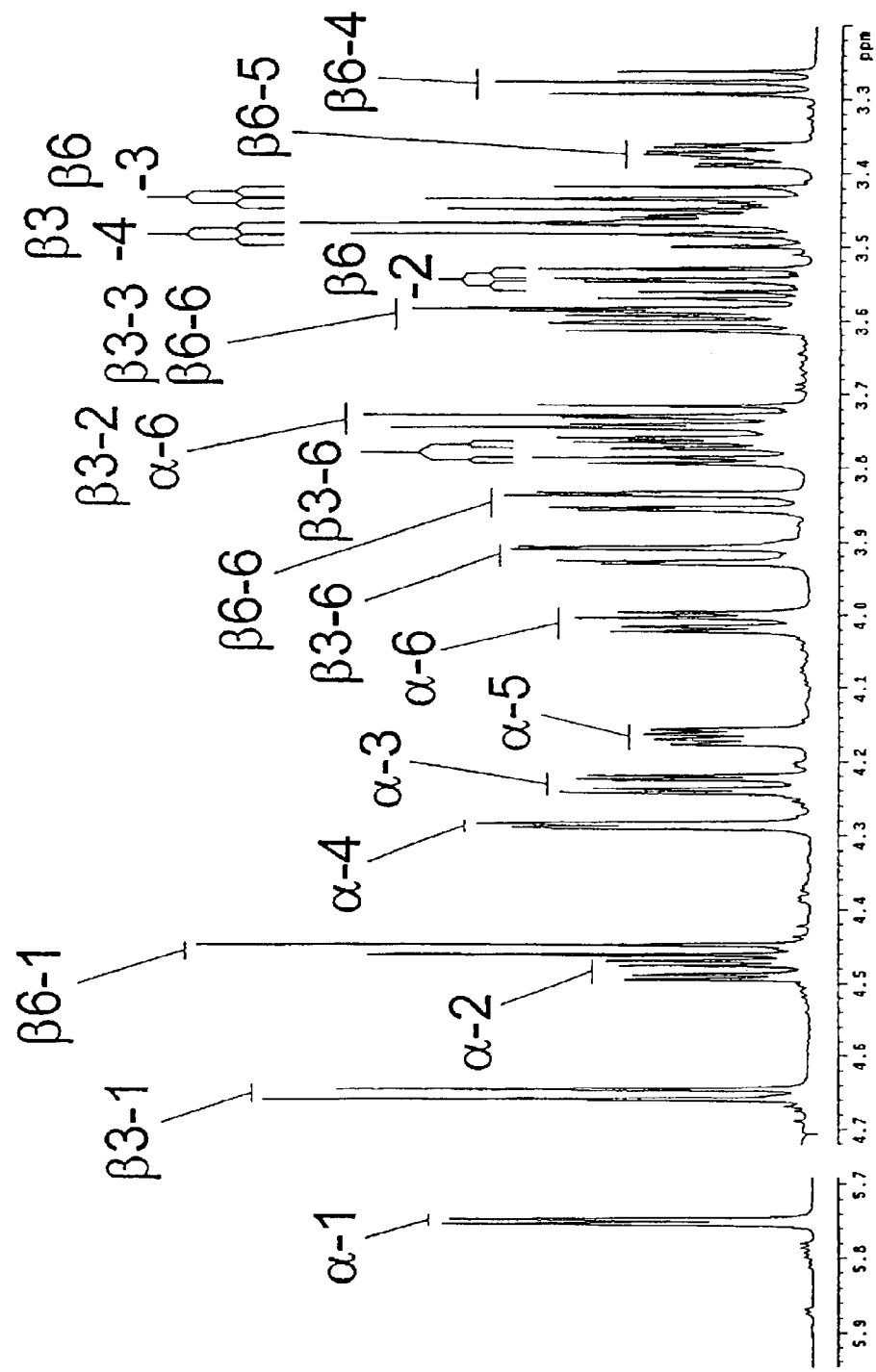
FIG. 5 depicts sections of a 1-D 1H-NMR spectrum of the C2/4GnT product GlcNAcβ1-3(GlcNAcβ1-6)GalNAcα1-1-pNph, showing all non-exchangeable monosaccharide ring methine and exocyclic methylene resonances. Residue designations for GlcNAcβ1→3 (β3), GlcNAcβ1→6 (β6), and GalNAcα1→1 (α) are followed by proton designations (1–6). All resonances in this region except for β3–5 (3.453 ppm) are marked.

Human multiple tissue northern blots containing mRNA from healthy human adult organs (Clontech) were probed with a C2/4GnT-probe. Northern analysis with mRNA from sixteen organs showed expression of C2/4GnT in organs of the gastrointestinal tract with high transcription levels observed in colon and kidney and lower levels in small intestine and pancreas (FIG. 4A). To investigate changes in expression of C2/4GnT in cancer cells derived from tissues normally expressing C2/4GnT, mRNA levels in a panel of human adenocarcinoma cell lines were determined. Analyses of C2/4GnT transcription levels revealed differential expression in pancreatic cell lines: Capan-1 and AsPC-1 expressed the transcript, whereas PANC-1, Capan-2, and BxPC-3 did not (FIG. 4B). Of the colonic cell lines, only HT-29 expressed transcripts of C2/4GnT. The size of the predominant transcript was approximately 2.4 kilobases, which correlates to the transcript size of 2.1 kilobases of the smallest of three transcripts of human C2GnT (12). Additionally, transcripts of approximately 3.4 kilobases and 6 kilobases were obtained in mRNA from healthy colonic mucosa (FIG. 4A). The two additional transcripts may resemble the 3.3 kilobase and 5.4 kilobase transcripts of C2GnT, which have not yet been characterized. Multiple transcripts of C2GnT have been suggested to be caused by differential usage of polyadenylation signals, which affects the length of the 3' UTR (12).

Genomic Organization of C2/4GnT Gene.

Figure 6:
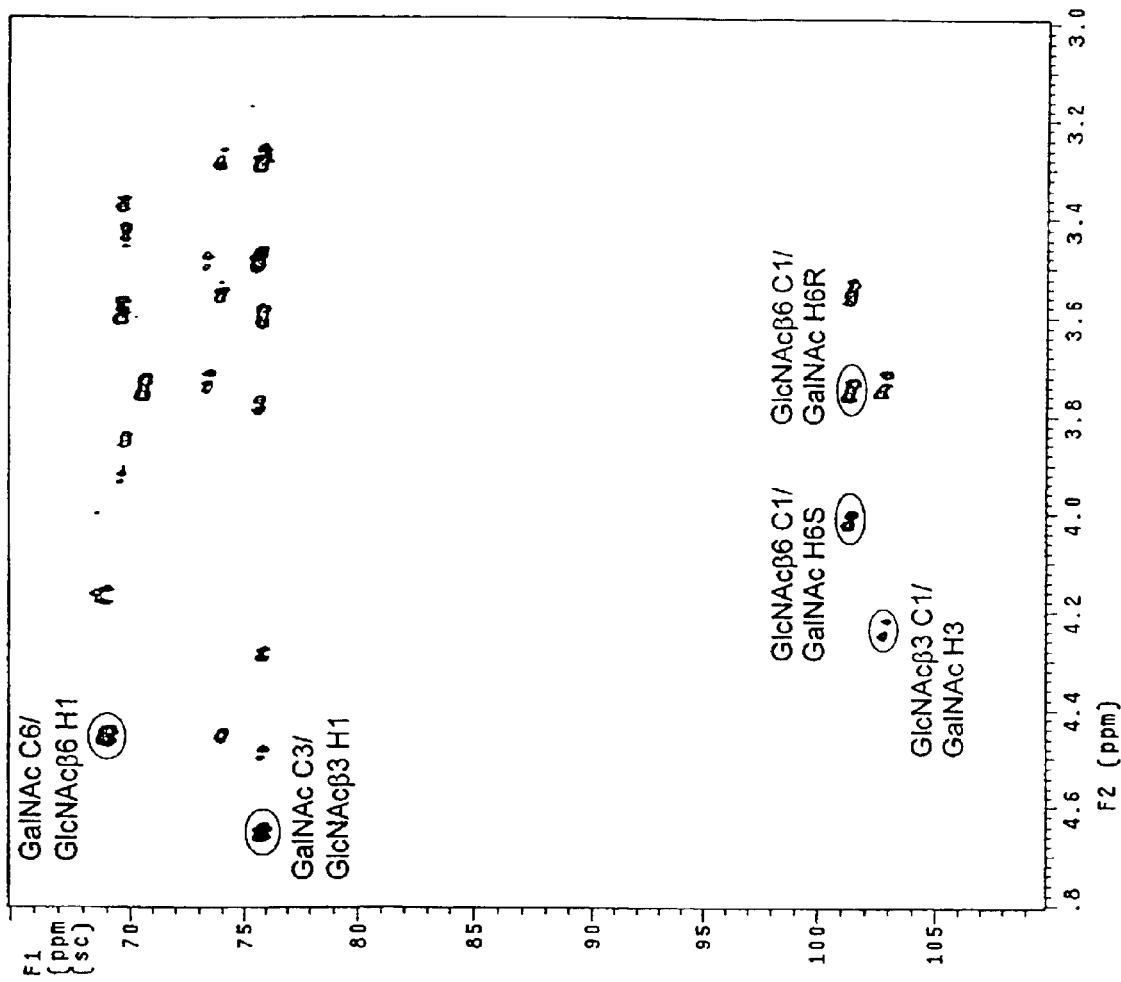
FIG. 6 is a section of the $^1$H-detected $^1$H—$^{13}$C heteronuclear multiple bond correlation (HMBC) spectrum of the Core 4 β6 GlcNAc transferase product, showing interglycosidic H1-C1-O1-Cx and C1-O1-Cx-Hx correlations (cross-peaks marked by ovals). The unmarked cross-peaks are all intra-residue correlations.

The present invention also provides isolated genomic DNA molecules encoding C2/4GnT. A human genomic foreskin P1 library (DuPont Merck Pharmaceutical Co. Human Foreskin Fibroblast P1 Library) by screening with the primer pair TSHC27 (5'-GGAAGTTCATACAGTTCCCAC-3') (SEQ ID NO:3) and TSHC28 (5'-CCTCCCATTCAACATCTTGAG-3') (SEQ ID NO:4), located in the coding exon yielding a product of 400 bp. Two genomic clones for C2/4GnT, DPMC-HFF#1-1026 (E2) and DPMC-HFF#1-1091(F1) were obtained from Genome Systems Inc. The P1 clone was partially sequenced and introns in the 5'-untranslated region of C2/4GnT mRNA identified as shown in FIG. 6. All exon/intron boundaries identified conform to the GT-AG consensus rule.

Chromosomal Localization of C2/4GnT Gene.

Figure 7:
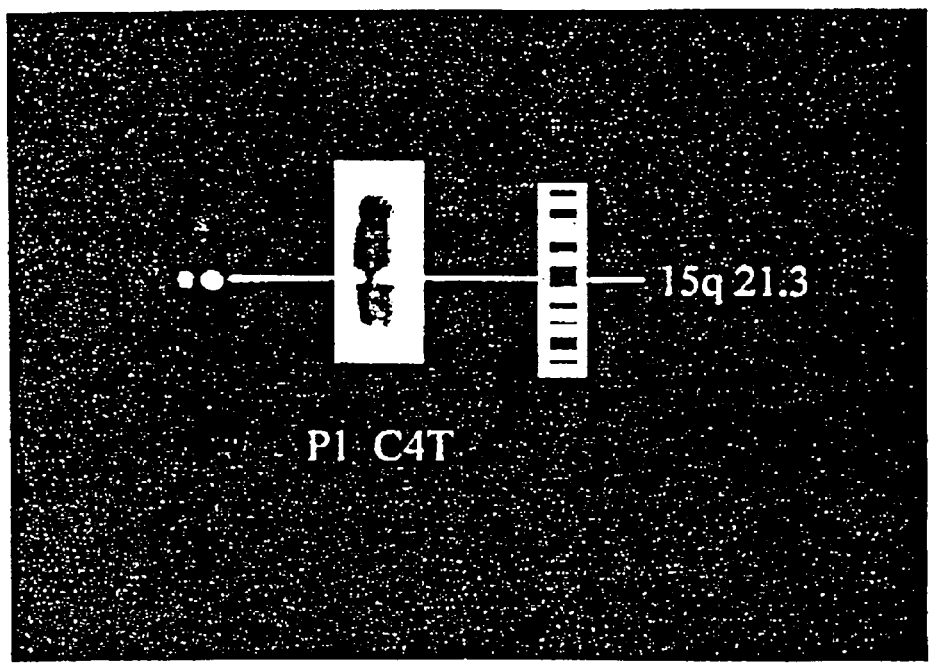
FIG. 7 shows a fluorescence in situ hybridization of C2/4GnT to metaphase chromosomes. The C2/4GnT probe (P1 DNA from clone DPMC-HFF#1-1091[F1]) labeled band 15q21.3

The present invention also discloses the chromosomal localization of the C2/4GnT gene. Fluorescence in situ hybridization to metaphase chromosomes using the isolated P1 phage clone DPMC-HFF#1-1091(F1) showed a fluorescence signal at 15q21.3 (FIG. 7; 20 metaphases evaluated). No specific hybridization was observed at any other chromosomal site.

The C2/4GnT gene is selectively expressed in organs of the gastrointestinal tract. The C2/4GnT enzyme of the present invention was shown to exhibit O-glycosylation capacity implying that the C2/4GnT gene is vital for correct/full O-glycosylation in vivo as well. A structural defect in the C2/4GnT gene leading to a deficient enzyme or completely defective enzyme would therefore expose a cell or an organism to protein/peptide sequences which were not covered by O-glycosylationas seen in cells or organisms with intact C2/4GnT gene. Described in Example 6 below is a method for scanning the coding exon for potential structural defects. Similar methods could be used for the characterization of defects in the non-coding region of the C2/4GnT gene including the promoter region.

DNA, Vectors, and Host Cells

In practicing the present invention, many conventional techniques in molecular biology, microbiology, recombinant DNA, and immunology, are used. Such techniques are well known and are explained fully in, for example, Sambrook et al., 1989, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*, the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively); *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.) and *Handbook of Experimental Immunology*, 1986, Volumes I–IV (Weir and Blackwell eds.).

The invention encompasses isolated nucleic acid fragments comprising all or part of the nucleic acid sequence disclosed herein as set forth in SEQ ID NO:1 and FIG. 2. The fragments are at least about 8 nucleotides in length, preferably at least about 12 nucleotides in length, and most preferably at least about 15–20 nucleotides in length. The invention further encompasses isolated nucleic acids comprising sequences that are hybridizable under stringency conditions of 2×SSC, 55 C, to the nucleotide sequence set forth in SEQ ID NO:1 and FIG. 2; preferably, the nucleic acids are hybridizable at 2×SSC, 65° C.; and most preferably, are hybridizable at 0.5×SSC, 65° C.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural human regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

According to the present invention, useful probes comprise a probe sequence at least eight nucleotides in length that consists of all or part of the sequence from among the sequences as set forth in FIG. 2 or sequence-conservative or function-conservative variants thereof, or a complement thereof, and that has been labelled as described above.

The invention also provides nucleic acid vectors comprising the disclosed sequence or derivatives or fragments thereof A large number of vectors, including plasmid and fungal vectors, have been described for replication and/or expression in a variety of eukaryotic and prokaryotic hosts, and may be used for gene therapy as well as for simple cloning or protein expression.

Recombinant cloning vectors will often include one or more replication systems for cloning or expression, one or more markers for selection in the host, e.g. antibiotic resistance, and one or more expression cassettes. The inserted coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ mediated DNA uptake, fungal infection, microinjection, microprojectile, or other established methods.

Appropriate host cells included bacteria, archebacteria, fungi, especially yeast, and plant and animal cells, especially mammalian cells. Of particular interest are *Saccharomyces cerevisiae, Schizosaccharomyces pombe, Pichia pastoris, Hansenula polymorpha, Neurospora*, SF9 cells, C129 cells, 293 cells, and CHO cells, COS cells, HeLa cells, and immortalized mammalian myeloid and lymphoid cell lines.

Preferred replication systems include M13, ColE1, 2, ARS, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation manner of manipulation, etc. are known in the art. Under appropriate expression conditions, host cells can be used as a source of recombinantly produced C2/4GnT derived peptides and polypeptides.

Advantageously, vectors may also include a transcription regulatory element (i.e., a promoter) operably linked to the C2/4GnT coding portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; arabinose BAD operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3 phosphate dehydrogenase (GAPDH) promoter, galactokinase (GAL1) promoter, galactoepimerase (GAL10) promoter, (CUP) copper cch and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are known in the art.

Nucleic acids encoding wild type or variant polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use, for example, as probes for the detection of C2/4GnT in other species or related organisms and as templates for the recombinant production of peptides or polypeptides. These and other embodiments of the present invention are described in more detail below.

Polypeptides and Antibodies

The present invention encompasses isolated peptides and polypeptides encoded by the disclosed genomic sequence. Peptides are preferably at least five residues in length.

Nucleic acids comprising protein-coding sequences can be used to direct the recombinant expression of polypeptides in intact cells or in cell-free translation systems. The known genetic code, tailored if desired for more efficient expression in a given host organism, can be used to synthesize oligo-nucleotides encoding the desired amino acid sequences. The phosphoramidite solid support method of Matteucci et al., 1981, *J. Am. Chem. Soc.* 103:3185, the method of Yoo et al., 1989, *J. Biol. Chem.* 764:17078, or other well known methods can be used for such synthesis. The resulting oligonucleotides can be inserted into an appropriate vector and expressed in a compatible host organism.

The polypeptides of the present invention, including function-conservative variants of the sequence disclosed in SEQ ID NO:2, may be isolated from native or from heterologous organisms or cells (including, but not limited to, bacteria, fungi, insect, plant, and mammalian cells) into which a protein-coding sequence has been introduced and expressed. Furthermore, the polypeptides may be part of recombinant fusion proteins.

Methods for polypeptide purification are well known in the art, including, without limitation, preparative discontinues gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

The present invention also encompasses derivatives and homologues of polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention encompasses antibodies that specifically recognize immunogenic components derived from C2/4GnT. Such antibodies can be used as reagents for detection and purification of C2/4GnT.

C2/4GnT specific antibodies according to the present invention include polyclonal and monoclonal antibodies. The antibodies may be elicited in an animal host by immunization with C2/4GnT components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies. Methods for the production of all of the above types of antibodies and derivatives are well known in the art. For example, techniques for producing and processing polyclonal antisera are disclosed in Mayer and Walker, 1987, *Immunochemical Methods in Cell and Molecular Biology*, (Academic Press, London).

The antibodies of this invention can be purified by standard methods, including but not limited to preparative disc-gel electrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification,* 1989, Amicon Division, W.R. Grace & Co. General protein purification methods are described in *Protein Purification: Principles and Practice,* R. K. Scopes, Ed., 1987, Springer-Verlag, New York, N.Y.

Anti C2/4GnT antibodies, whether unlabeled or labeled by standard methods, can be used as the basis for immunoassays. The particular label used will depend upon the type of immunoassay used. Examples of labels that can be used include, but are not limited to, radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described in, e.g., Chan (Ed.), 1987, *Immunoassay: A Practical Guide*, Academic Press, Inc., Orlando, Fla.

Core 2 O-glycans are involved in cell-cell adhesion events through selectin binding, and the core 2 beta6GlcNAc-transferase activity is required for synthesis of the selectin ligands (11). The core 2 beta6GlcNAc-transferase activity therefore plays a major role in selectin mediated cell trafficking including cancer metastasis. Since at least two different core 2 synthases exist it is required to define which of these are involved in synthesis of O-glycans in different cell types and in disease. Development of inhibitors of individual or all core 2 synthase activities may be usefull in reducing or eliminating core 2 O-glycans in cells and tissues, and hence inhibiting the biological events these ligands are involved in. Inhibition of transcription and/or translation of core 2 beta6GlcNAc-transferase genes may have the same effect. Compounds with such effects may be used as drugs with anti-inflammatory activity and/or for treatment of cancer growth and spreading.

The following examples are intended to further illustrate the invention without limiting its scope.

EXAMPLE 1

A: Identification of cDNA Homologous to C2/4GnT by Analysis of EST Database Sequence Information.

Database searches were performed with the coding sequence of the human C2GnT sequence ( ) using the BLASTn and tBLASTn algorithms against the dbEST database at The National Center for Biotechnology Information, USA. The BLASTn algorithm was used to identify ESTs representing the query gene (identities of 95%), whereas tBLASTn was used to identify non-identical, but similar EST sequences. ESTs with 50–90% nucleotide sequence identity were regarded as different from the query sequence. Composites of all the sequence information for each set of ESTs were compiled and analysed for sequence similarity to human C2GnT.

B: Cloning and Sequencing of C2/4GnT.

EST clone 178656 (5' EST GenBank accession number AA307800), derived from a putative homologue to C2GnT, was obtained from the American Type Culture Collection, USA. Sequencing of this clone revealed a partial open reading frame with significant sequence similarity to C2GnT. The coding region of human C2GnT and a bovine homologue was previously found to be organized in one exon (13) and unpublished observations). Since the 5' and 3' sequence available from the C2/4GnT EST was incomplete but likely to be located in a single exon, the missing 5' and 3' portions of the open reading frame was obtained by sequencing genomic P1 clones. P1 clones were obtained from a human foreskin genomic P1 library (DuPont Merck Pharmaceutical Co. Human Foreskin Fibroblast P1 Library) by screening with the primer pair TSHC27 (5'-GGAAGTTCATACAGTTCCCAC-3') (SEQ ID NO:3) and TSHC28 (5'-CCTCCCATTCAACATCTTGAG -3') (SEQ ID NO:4). Two genomic clones for C2/4GnT, DPMC-HFF#1-1026(E2) and DPMC-HFF#1-1091(F1) were obtained from Genome Systems Inc. DNA from P1 phage was prepared as recommended by Genome Systems Inc. The entire coding sequence of the C2/4GnT gene was represented in both clones and sequenced in full using automated sequencing (ABI377, Perkin-Elmer). Confirmatory sequencing was performed on a cDNA clone obtained by PCR (30 cycles at 95° C. for 15 sec; 55° C. for 20 sec and 68° C. for 2 min 30 sec) on total cDNA from the human COLO 205 cancer cell line with the sense primer TSHC54 (5'-GCAGAATTCATGGTTCAATGGAAGAGACTC-3') (SEQ ID NO:7) and the anti-sense primer TSHC45 (5'-AGCGAATTCAGCTCAAAGTTCAGTCCCATAG-3') (SEQ ID NO:5). The composite sequence contained an open reading frame of 1314 base pairs encoding a putative protein of 438 amino acids with type II domain structure predicted by the TMpred-algorithm at the Swiss Institute for Experimental Cancer Research (ISREC) (http:flwww.isrec.isb-sib.ch/software/TMPRED_form.html). The sequence of the 5'-end of C2/4GnT mRNA including the translational start site and 5'-UTR was obtained by 5' rapid amplification of cDNA ends (35 cycles at 94° C. for 20 sec; 52° C. for 15 sec and 72° C. for 2 min) using total cDNA from the human COLO 205 cancer cell line with the anti-sense primer TSHC48 (5'-GTGGGAACTGTATGAACTTCC-3') (SEQ ID NO:6) (FIG. 2).

EXAMPLE 2

A: Expression of C2/4GnT in Sf9 Cells.

An expression construct designed to encode amino acid residues 31–438 of C2/4GnT was prepared by PCR using P1 DNA, and the primer pair TSHC55 (5'-CGAGAATTCAGGTTGAAGTGTGACTC -3') (SEQ ID NO:8) and TSHC45 (SEQ ID NO:5) (FIG. 2). The PCR product was cloned into the EcoRI site of pAcGP67A (PharMingen), and the insert was fully sequenced. Plasmids pAcGP67-C2/4GnT-sol and pAcGP67-C2GnT-sol were co-transfected with Baculo-Gold™ DNA (PharMingen) as described previously (14). Recombinant Baculo-virus were obtained after two successive amplifications in Sf9 cells grown in serum-containing medium, and titers of virus were estimated by titration in 24-well plates with monitoring of enzyme activities. Controls included the pAcGP67-GalNAc-T3-sol (15).

B: Analysis of C2/4GnT Activity.

Standard assays were performed using culture supernatant from infected cells in 50 μl reaction mixtures containing 100 mM MES (pH 8.0), 10 mM EDTA, 10 mM 2-Acetamido-2-deoxy-D-glucono-1,5-lacton, 180 μM UDP-[$^{14}C$]-GlcNAc (6,000 cpm/nmol) (Amersham Pharmacia Biotech), and the indicated concentrations of acceptor substrates (Sigma and Toronto Research Laboratories Ltd., see Table I for structures). Semi-purified C2/4GnT was assayed in 50 μl reaction mixtures containing 100 mM MES (pH 7), 5 mM EDTA, 90 μM UDP-[$^{14}$C]-GlcNAc (3,050 cpm/nmol) (Amersham Pharmacia Biotech), and the indicated concentrations of acceptor substrates. Reaction products were quantified by chromatography on Dowex AG1-X8.

EXAMPLE 3
Restricted Organ Expression Pattern of C2/4GnT

Total RNA was isolated from human colon and pancreatic adenocarcinoma cell lines AsPC-1, BxPC-3, Capan-1, Capan-2, COLO 357, HT-29, and PANC-1 essentially as described (17). Twenty five μg of total RNA was subjected to electrophoresis on a 1% denaturing agarose gel and transferred to nitrocellulose as described previously (17). The cDNA-fragment of soluble C2/4GnT was used as a probe for hybridization. The probe was random primer-labeled using [α$^{32}$P]dCTP and an oligonucleotide labeling kit (Amersham Pharmacia Biotech). The membrane was probed overnight at 42° C. as described previously (15), and washed twice for 30 min each at 42° C. with 2×SSC, 0.1% SDS and twice for 30 min each at 52° C. with 0.1×SSC, 0.1 % SDS. Human 20 multiple tissue Northern blots, MTN I and MTN II (CLONTECH), were probed as described above and washed twice for 10 min each at room temperature with 2×SSC, 0.1% SDS; twice for 10 min each at 55° C. with 1×SSC, 0.1 % SDS; and once for 10 min with 0.1×SSC, 0.1% SDS at 55° C.

EXAMPLE 4
Genomic Structure of the Coding Region of C2/4GnT

Human genomic clones were obtained from a human foreskin genomic P1 library (DuPont Merck Pharmaceutical Co. Human Foreskin Fibroblast P1 Library) by screening with the primer pair TSHC27 (5'-GGAAGTTCATACAGTTCCCAC-3') (SEQ ID NO:3) and TSHC28 (5'-CCTCCCATTCAACATCTTGAG -3') (SEQ ID NO:4). Two genomic clones for C2/4GnT, DPMC-HFF#1-1026(E2) and DPMC-HFF#1-1091(F1) were obtained from Genome Systems Inc. DNA from P1 phage was prepared as recommended by Genome Systems Inc. The entire coding sequence of the C2/4GnT gene was represented in both clones and sequenced in full using automated sequencing (ABI377, Perkin-Elmer). Intron/exon boundaries were determined by comparison with the cDNA sequences optimising for the gt/ag rule (Breatdnach and Chambon, 1981).

EXAMPLE 5
Chromosomal Localization of C2/4GnT: In Situ Hybridization to Metaphase Chromosomes P1 DNA was labeled with biotin-14-dATP using the bio-NICK system (Life Technologies). The labeled DNA was precipitated with ethanol in the presence of herring sperm DNA. Precipitated DNA was dissolved and denatured at 80 C for 10 min followed by incubation for 30 min at 37 C and added to heat-denatured chromosome spreads where hybridization was carried out over night in a moist chamber at 37 C After posthybridization washing (50% formamide, 2×SSC at 42 C) and blocking with nonfat dry milk powder, the hybridized probe was detected with avidin-FITC (Vector Laboratories) followed by two amplification steps using rabbit-anti-FITC (Dako) and mouse-anti-rabbit FITC (Jackson Immunoresearch). Chromosome spreads were mounted in antifade solution with blue dye DAPI.

EXAMPLE 6
Analysis of DNA Polymorphism of C2/4GnT Gene

Figure 8:
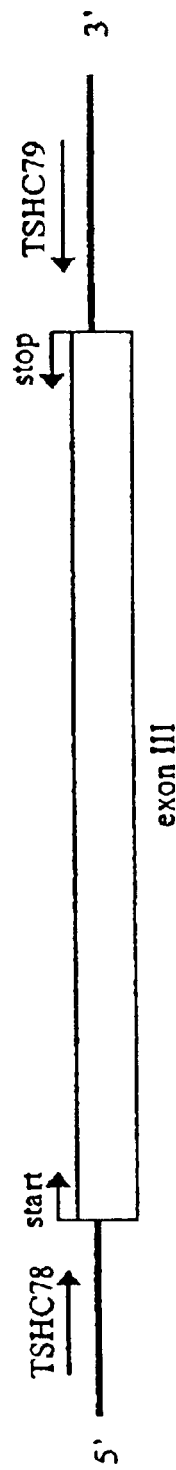
FIG. 8 is a schematic representation of forward (TSHC78) and reverse (TSHC79) PCR primers that can be used to amplify the coding exon of the C2/4GnT gene. The sequences of the primers are also shown. TSHC78 has SEQ ID NO:9 and TSHC79 has SEQ ID NO:10.

Primer pairs as described in FIG. 8 have been used for PCR amplification of individual sequences of the coding exon III. Each PCR product was subcloned and the sequence of 10 clones containing the appropriate insert was determined assuring that both alleles of each individual are characterized.

From the foregoing it will be evident that, although specific embodiments of the invention have been described herein for purposes of illustration, various modifications may be made without deviating from the spirit and scope of the invention.

References

1. Clausen, H. and Bennett, E. P. A family of UDP-GalNAc: polypeptide N-acetylgalactosaminyl-transferases control the initiation of mucin-type O-linked glycosylation. Glycobiology, 6: 635–646, 1996.

2. Piller, F., Piller, V., Fox, R. I., and Fukuda, M. Human T-lymphocyte activation is associated with changes in O-glycan biosynthesis. J.Biol.Chem., 263: 15146–15150, 1988.

3. Yang, J. M., Byrd, J. C., Siddiki, B. B., Chung, Y. S., Okuno, M., Sowa, M., Kim, Y. S., Matta, K. L., and Brockhausen, I. Alterations of O-glycan biosynthesis in human colon cancer tissues. Glycobiology, 4: 873–884, 1994.

4. Yousefi, S., Higgins, E., Daoling, Z., Pollex-Kruger, A., Hindsgaul, O., and Dennis, J. W. Increased UDP-GlcNAc:Gal beta 1-3GalNAc-R (GlcNAc to GalNAc) beta-1,6- N-acetylglucosaminyltransferase activity in metastatic murine tumor cell lines. Control of polylactosamine synthesis. J.Biol.Chem., 266:1772–1782, 1991.

5. Fukuda, M. Possible roles of tumor-associated carbohydrate antigens. Cancer Res., 56: 2237–2244, 1996.

6. Brockhausen, I., Yang, J. M., Burchell, J., Whitehouse, C., and Taylor-Papadimitriou, J. Mechanisms underlying aberrant glycosylation of MUC1 mucin in breast cancer cells. Eur.J.Biochem., 233:607–617, 1995.

7. Brockhausen, I., Kuhns, W., Schachter, H., Matta, K. L., Sutherland, D. R., and Baker, M. A. Biosynthesis of O-glycans in leukocytes from normal donors and from patients with leukemia: increase in O-glycan core 2 UDP-GlcNAc:Gal beta 3 GalNAc alpha-R (GlcNAc to GalNAc) beta(1-6)-N-acetylglucosaminyltransferase in leukemic cells. Cancer Res., 51: 1257–1263, 1991.

8. Higgins, E. A., Siminovitch, K. A., Zhuang, D. L., Brockhausen, I., and Dennis, J. W. Aberrant O-linked oligosaccharide biosynthesis in lymphocytes and platelets from patients with the Wiskott-Aldrich syndrome. J.Biol.Chem., 266: 6280–6290, 1991.

9. Saitoh, O., Piller, F., Fox, R. I., and Fukuda, M. T-lymphocytic leukemia expresses complex, branched O-linked oligosaccharides on a major sialoglycoprotein, leukosialin. Blood, 77: 1491–1499, 1991.

10. Springer, G. F. T and Tn, general carcinoma autoantigens. Science, 224: 1198–1206, 1984.

11. Kumar, R., Camphausen, R. T., Sullivan, F. X., and Cumming, D. A. Core2 beta-1,6-N-acetylglucosaminyltransferase enzyme activity is critical for P-selectin glycoprotein ligand-1 binding to P-selectin. Blood, 88: 3872–3879, 1996.

12. Bierhuizen, M. F. and Fukuda, M. Expression cloning of a cDNA encoding UDP-GlcNAc:Gal beta 1-3-GalNAc-R (GlcNAc to GalNAc) beta 1-6GlcNAc transferase by gene transfer into CHO cells expressing polyoma large tumor antigen. Proc.Natl.Acad.Sci.U.S.A., 89: 9326–9330, 1992.

13. Bierhuizen, M. F., Maemura, K., Kudo, S., and Fukuda, M. Genomic organization of core 2 and I branching beta-1,6-N-acetylglucosaminyltransferases. Implication for evolution of the beta- 1,6-N-acetylglucosaminyltransferase gene family. Glycobiology, 5: 417425, 1995.

14. Almeida, R., Amado, M., David, L., Levery, S. B., Holmes, E. H., Merkx, G., van Kessel, A. G., Rygaard, E., Hassan, H., Bennett, E., and Clausen, H. A family of human beta4-galactosyltransferases. Cloning and expression of two novel UDP-galactose:beta-n-acetylglucosamine beta1, 4-galactosyltransferases, beta4Gal-T2 and beta4Gal-T3. J.Biol.Chem., 272:31979–31991, 1997.

15. Bennett, E. P., Hassan, H., and Clausen, H. cDNA cloning and expression of a novel human UDP-N-acetyl-alpha-D-galactosamine. Polypeptide N-acetylgalactos-aminyltransferase, GalNAc-t3. J.Biol.Chem., 271: 17006–17012, 1996.

16. Wandall, H. H., Hassan, H., Mirgorodskaya, E., Kristensen, A. K., Roepstorff, P., Bennett, E. P., Nielsen, P. A., Hollingsworth, M. A., Burchell, J., Taylor-Papadimitriou, J., and Clausen, H. Substrate specificities of three members of the human UDP-N-acetyl- alpha-D-galactosamine:Polypeptide N-acetylgalactosaminyl-transferase family, GalNAc-T1, -T2, and -T3. J.Biol.Chem., 272: 23503–23514, 1997.

17. Sutherlin, M. E., Nishimori, I., Caffrey, T., Bennett, E. P., Hassan, H., Mandel, U., Mack, D., Iwamura, T., Clausen, H., and Hollingsworth, M. A. Expression of three UDP-N-acetyl-alpha-D-galactosamine:polypeptide GalNAc N-acetylgalactos-aminyltransferases in adenocarcinoma cell lines. Cancer Res., 57: 4744–4748, 1997.

---

What is claimed is:

1. An isolated nucleic acid encoding UDP-N-acetylglucosamine: galactose-β1,3-N-acetylgalactosamine-α-R/N-acetylglucosainine-β1,3-N-acetylgalactosamine-α-R β1,6-N-acetylglucosaminyltransferase (C2/4GnT) having the amino acid sequence SEQ ID NO: 2 or an enzymatically active fragment thereof.

2. An isolated nucleic acid as defined in claim 1, wherein said nucleic acid is DNA.

3. An isolated nucleic acid as defined in claim 2, wherein said DNA is cDNA.

4. An isolated nucleic acid as defined in claim 2, wherein said DNA is genomic DNA.

5. An isolated nucleic acid encoding UDP-N-acetylglucosamine: galactose-β1,3-N-acetylgalactosamine-α-R/N-acetylglucosamine-β1,3-N-acetylgalactosamine-α-R β1,6-N-acetylglucosaminyl-transferase (C2/4GnT), wherein said nucleic acid comprises the sequence of nucleotides 1–2319 in SEQ ID NO:1 or sequence-conservative variants thereof.

6. A nucleic acid vector comprising the nucleic acid of claim 1.

7. A vector as defined in claim 6, wherein said nucleic acid comprises the nucleotide sequence of nucleotides 1-2319 in SEQ ID NO: 1 or sequence-conservative variants thereof.

8. A vector as defined in claim 7, wherein said sequence encoding C2/4GnT is operably linked to a transcriptional regulatory element.

9. A cell comprising a vector as defined in claim 6.

10. A cell comprising a vector as defined in claim 8.

11. A cell as defined in claim 10, wherein said cell is stably transfected with said vector.

12. A cell as defined in claim 9, wherein said cell produces enzymatically active C2/4GnT.

13. A cell as defined in claim 9, wherein said cell is selected from the group consisting of bacterial, yeast, insect, avian, and mammalian cells.

14. A cell as defined in claim 12, wherein said cell is selected from the group consisting of bacterial, yeast, insect, avian, and mammalian cells.

15. A cell as defined in claim 14, wherein said cell is Sf9.

16. A cell as defined in claim 14, wherein said cell is CHO.

17. A method for the identification of DNA sequence variations in a region of the C2/4GnT gene, comprising the steps of:
  (i) isolating DNA from a patient;
  (ii) amplifying by PCR a segment of the patient's DNA using amplification primers capable of amplifying a subsequence of SEQ ID NO: 1, said sequence consisting of a fragment of a nucleotide sequence selected from the group consisting of nucleotides 1-245, nucleotides 246-435, and nucleotides 436-2319 SEQ ID NO: 1; and
  (iii) detecting the presence of DNA sequence variation in the amplified segment compared to said subsequence of SEQ ID NO: 1 by DNA sequencing or single strand conformational polymorphism (SSCP).

18. An isolated nucleic acid as defined in claim 1, wherein said nucleic acid comprises the nucleotide sequence of nucleotides 496–1812 in SEQ ID NO:1 or sequence-conservative variants thereof.

19. An isolated nucleic acid as defined in claim 1, wherein said nucleic acid comprises the nucleotide sequence of nucleotides 634–1812 in SEQ ID NO:1 or sequence-conservative variants thereof.

20. A method for screening for DNA sequence variations in a region of the human C2/4GnT gene comprising the steps of:
  (i) amplifying a segment of genomic DNA obtained from a human subject, using amplification primers capable of amplifying a subsequence of SEQ ID NO: 1, said subsequence consisting of a fragment of a nucleotide sequence selected from the group consisting of nucleotides 1–245, nucleotides 246–435, and nucleotides 436–2319 of SEQ ID NO: 1; and
  (ii) comparing the sequence of the amplified segment with said subsequence of SEQ ID NO: 1 and identifying the differences between the sequence of said segment and said subsequence of SEQ ID NO:1.

21. A nucleic acid vector comprising the nucleic acid of claim 18.

22. A nucleic acid vector comprising the nucleic acid of claim 19.

23. A cell comprising a vector as defined in claim 21.

24. A cell comprising a vector as defined in claim 22.

* * * * *

SEQUENCE LISTING

```
<160> NUMBER OF SEQ ID NOS: 12

<210> SEQ ID NO 1
<211> LENGTH: 2319
<212> TYPE: DNA
<213> ORGANISM: Homo sapiens
<220> FEATURE:
<221> NAME/KEY: CDS
<222> LOCATION: (496)..(1809)
<223> OTHER INFORMATION:

<400> SEQUENCE: 1
attaactggg ttttcctatt tatctatcct ctcgcattac ttctctgagt cagagcctct     60
tctctctaag tcacgggaac tgcccttgct acttgtgacc tgcccttac tcagcagttt    120 ttgttctggg aagccctggg attctgctaa tacctatcac tgtaggtgct gaagggaaac    180
agatgaagaa catgacctca aggagcttcc tgtcaatgag aagaccaagc tgacgcctgg    240
caaagatatt aaagaggagc ctgaaactgt tccttggaca tcttatgaat gtcagaaaat    300 acctttttgga gggttagaag atcaggggac atggttgttc acatttgctg ccacggaaca    360
ccgccagtct tcacttggaa acagaatcac gccttgtgaa gagatcatcc ctaagcagga    420
gagaagctac taaaggattg tgtcctcctc caccttccct gtgctcggtc tccacctgtc    480
tcccattctg tgacg atg gtt caa tgg aag aga ctc tgc cag ctg cat tac    531
              Met Val Gln Trp Lys Arg Leu Cys Gln Leu His Tyr
                1               5                   10 ttg tgg gct ctg ggc tgc tat atg ctg ctg gcc act gtg gct ctg aaa    579
Leu Trp Ala Leu Gly Cys Tyr Met Leu Leu Ala Thr Val Ala Leu Lys
         15                  20                  25 ctt tct ttc agg ttg aag tgt gac tct gac cac ttg ggt ctg gag tcc    627
Leu Ser Phe Arg Leu Lys Cys Asp Ser Asp His Leu Gly Leu Glu Ser
     30                  35                  40 agg gaa tct caa agc cag tac tgt agg aat atc ttg tat aat ttc ctg    675
Arg Glu Ser Gln Ser Gln Tyr Cys Arg Asn Ile Leu Tyr Asn Phe Leu
 45                  50                  55                  60 aaa ctt cca gca aag agg tct atc aac tgt tca ggg gtc acc cga ggg    723
Lys Leu Pro Ala Lys Arg Ser Ile Asn Cys Ser Gly Val Thr Arg Gly
                 65                  70                  75 gac caa gag gca gtg ctt cag gct att ctg aat aac ctg gag gtc aag    771
Asp Gln Glu Ala Val Leu Gln Ala Ile Leu Asn Asn Leu Glu Val Lys
             80                  85                  90 aag aag cga gag cct ttc aca gac acc cac tac ctc tcc ctc acc aga    819
Lys Lys Arg Glu Pro Phe Thr Asp Thr His Tyr Leu Ser Leu Thr Arg
         95                  100                 105
```

-continued

| | |
|---|---|
| gac tgt gag cac ttc aag gct gaa agg aag ttc ata cag ttc cca ctg<br>Asp Cys Glu His Phe Lys Ala Glu Arg Lys Phe Ile Gln Phe Pro Leu<br>110                      115                    120 | 867 |
| agc aaa gaa gag gtg gag ttc cct att gca tac tct atg gtg att cat<br>Ser Lys Glu Glu Val Glu Phe Pro Ile Ala Tyr Ser Met Val Ile His<br>125                  130                    135                    140 | 915 |
| gag aag att gaa aac ttt gaa agg cta ctg cga gct gtg tat gcc cct<br>Glu Lys Ile Glu Asn Phe Glu Arg Leu Leu Arg Ala Val Tyr Ala Pro<br>                  145                    150                    155 | 963 |
| cag aac ata tac tgt gtc cat gtg gat gag aag tcc cca gaa act ttc<br>Gln Asn Ile Tyr Cys Val His Val Asp Glu Lys Ser Pro Glu Thr Phe<br>                160                    165                    170 | 1011 |
| aaa gag gcg gtc aaa gca att att tct tgc ttc cca aat gtc ttc ata<br>Lys Glu Ala Val Lys Ala Ile Ile Ser Cys Phe Pro Asn Val Phe Ile<br>175                      180                    185 | 1059 |
| gcc agt aag ctg gtt cgg gtg gtt tat gcc tcc tgg tcc agg gtg caa<br>Ala Ser Lys Leu Val Arg Val Val Tyr Ala Ser Trp Ser Arg Val Gln<br>190                      195                    200 | 1107 |
| gct gac ctc aac tgc atg gaa gac ttg ctc cag agc tca gtg ccg tgg<br>Ala Asp Leu Asn Cys Met Glu Asp Leu Leu Gln Ser Ser Val Pro Trp<br>205                      210                    215                    220 | 1155 |
| aaa tac ttc ctg aat aca tgt ggg acg gac ttt cct ata aag agc aat<br>Lys Tyr Phe Leu Asn Thr Cys Gly Thr Asp Phe Pro Ile Lys Ser Asn<br>                  225                    230                    235 | 1203 |
| gca gag atg gtc cag gct ctc aag atg ttg aat ggg agg aat agc atg<br>Ala Glu Met Val Gln Ala Leu Lys Met Leu Asn Gly Arg Asn Ser Met<br>                240                    245                    250 | 1251 |
| gag tca gag gta cct cct aag cac aaa gaa acc cgc tgg aaa tat cac<br>Glu Ser Glu Val Pro Pro Lys His Lys Glu Thr Arg Trp Lys Tyr His<br>255                      260                    265 | 1299 |
| ttt gag gta gtg aga gac aca tta cac cta acc aac aag aag aag gat<br>Phe Glu Val Val Arg Asp Thr Leu His Leu Thr Asn Lys Lys Lys Asp<br>270                      275                    280 | 1347 |
| cct ccc cct tat aat tta act atg ttt aca ggg aat gcg tac att gtg<br>Pro Pro Pro Tyr Asn Leu Thr Met Phe Thr Gly Asn Ala Tyr Ile Val<br>285                      290                    295                    300 | 1395 |
| gct tcc cga gat ttc gtc caa cat gtt ttg aag aac cct aaa tcc caa<br>Ala Ser Arg Asp Phe Val Gln His Val Leu Lys Asn Pro Lys Ser Gln<br>                  305                    310                    315 | 1443 |
| caa ctg att gaa tgg gta aaa gac act tat agc cca gat gaa cac ctc<br>Gln Leu Ile Glu Trp Val Lys Asp Thr Tyr Ser Pro Asp Glu His Leu<br>                320                    325                    330 | 1491 |
| tgg gcc acc ctt cag cgt gca cgg tgg atg cct ggc tct gtt ccc aac<br>Trp Ala Thr Leu Gln Arg Ala Arg Trp Met Pro Gly Ser Val Pro Asn<br>335                      340                    345 | 1539 |
| cac ccc aag tac gac atc tca gac atg act tct att gcc agg ctg gtc<br>His Pro Lys Tyr Asp Ile Ser Asp Met Thr Ser Ile Ala Arg Leu Val<br>350                      355                    360 | 1587 |
| aag tgg cag ggt cat gag gga gac atc gat aag ggt gct cct tat gct<br>Lys Trp Gln Gly His Glu Gly Asp Ile Asp Lys Gly Ala Pro Tyr Ala<br>365                      370                    375                    380 | 1635 |
| ccc tgc tct gga atc cac cag cgg gct atc tgc gtt tat ggg gct ggg<br>Pro Cys Ser Gly Ile His Gln Arg Ala Ile Cys Val Tyr Gly Ala Gly<br>                  385                    390                    395 | 1683 |
| gac ttg aat tgg atg ctt caa aac cat cac ctg ttg gcc aac aag ttt<br>Asp Leu Asn Trp Met Leu Gln Asn His His Leu Leu Ala Asn Lys Phe<br>                400                    405                    410 | 1731 |
| gac cca aag gta gat gat aat gct ctt cag tgc tta gaa gaa tac cta<br>Asp Pro Lys Val Asp Asp Asn Ala Leu Gln Cys Leu Glu Glu Tyr Leu<br>415                      420                    425 | 1779 |

-continued

```
cgt tat aag gcc atc tat ggg act gaa ctt tgagacacac tatgagagcg    1829
Arg Tyr Lys Ala Ile Tyr Gly Thr Glu Leu
    430                 435 ttgctacctg tggggcaaga gcatgtacaa acatgctcag aacttgctgg gacagtgtgg  1889
gtgggagacc aggctttgc aattcgtggc atcctttagg ataagagggc tgctattaga   1949
ttgtgggtaa gtagatcttt tgccttgcaa attgctgcct gggtgaatgc tgcttgttct  2009 ctcacccta accctagtag ttcctccact aactttctca ctaagtgaga atgagaactg   2069
ctgtgatagg gagagtgaag gagggatatg tggtagagca cttgatttca gttgaatgcc  2129
tgctggtagc ttttccattc tgtggagctg ccgttcctaa taattccagg tttggtagcg  2189
tggaggagaa ctttgatgga aagagaacct tcccttctgt actgttaact taaaaataaa  2249
tagctcctga ttcaaagtat tacctctact ttttgcctag tatgccagaa ataatataaa  2309
tctaaacaga                                                        2319
```

<210> SEQ ID NO 2
<211> LENGTH: 438
<212> TYPE: PRT
<213> ORGANISM: Homo sapiens

<400> SEQUENCE: 2

```
Met Val Gln Trp Lys Arg Leu Cys Gln Leu His Tyr Leu Trp Ala Leu
1               5                   10                  15

Gly Cys Tyr Met Leu Leu Ala Thr Val Ala Leu Lys Leu Ser Phe Arg
                20                  25                  30

Leu Lys Cys Asp Ser Asp His Leu Gly Leu Glu Ser Arg Glu Ser Gln
            35                  40                  45

Ser Gln Tyr Cys Arg Asn Ile Leu Tyr Asn Phe Leu Lys Leu Pro Ala
        50                  55                  60

Lys Arg Ser Ile Asn Cys Ser Gly Val Thr Arg Gly Asp Gln Glu Ala
65                  70                  75                  80

Val Leu Gln Ala Ile Leu Asn Asn Leu Glu Val Lys Lys Arg Glu
                85                  90                  95

Pro Phe Thr Asp Thr His Tyr Leu Ser Leu Thr Arg Asp Cys Glu His
                100                 105                 110

Phe Lys Ala Glu Arg Lys Phe Ile Gln Phe Pro Leu Ser Lys Glu Glu
            115                 120                 125

Val Glu Phe Pro Ile Ala Tyr Ser Met Val Ile His Glu Lys Ile Glu
        130                 135                 140

Asn Phe Glu Arg Leu Leu Arg Ala Val Tyr Ala Pro Gln Asn Ile Tyr
145                 150                 155                 160

Cys Val His Val Asp Glu Lys Ser Pro Glu Thr Phe Lys Glu Ala Val
                165                 170                 175

Lys Ala Ile Ile Ser Cys Phe Pro Asn Val Phe Ile Ala Ser Lys Leu
            180                 185                 190

Val Arg Val Val Tyr Ala Ser Trp Ser Arg Val Gln Ala Asp Leu Asn
        195                 200                 205

Cys Met Glu Asp Leu Leu Gln Ser Ser Val Pro Trp Lys Tyr Phe Leu
    210                 215                 220

Asn Thr Cys Gly Thr Asp Phe Pro Ile Lys Ser Asn Ala Glu Met Val
225                 230                 235                 240

Gln Ala Leu Lys Met Leu Asn Gly Arg Asn Ser Met Glu Ser Glu Val
                245                 250                 255
```

```
Pro Pro Lys His Lys Glu Thr Arg Trp Lys Tyr His Phe Glu Val Val
        260                 265                 270

Arg Asp Thr Leu His Leu Thr Asn Lys Lys Asp Pro Pro Tyr
        275                 280             285

Asn Leu Thr Met Phe Thr Gly Asn Ala Tyr Ile Val Ala Ser Arg Asp
        290                 295                 300

Phe Val Gln His Val Leu Lys Asn Pro Lys Ser Gln Gln Leu Ile Glu
305                 310                 315                 320

Trp Val Lys Asp Thr Tyr Ser Pro Asp Glu His Leu Trp Ala Thr Leu
                325                 330                 335

Gln Arg Ala Arg Trp Met Pro Gly Ser Val Pro Asn His Pro Lys Tyr
            340                 345                 350

Asp Ile Ser Asp Met Thr Ser Ile Ala Arg Leu Val Lys Trp Gln Gly
                355                 360                 365

His Glu Gly Asp Ile Asp Lys Gly Ala Pro Tyr Ala Pro Cys Ser Gly
        370                 375                 380

Ile His Gln Arg Ala Ile Cys Val Tyr Gly Ala Gly Asp Leu Asn Trp
385                 390                 395                 400

Met Leu Gln Asn His His Leu Leu Ala Asn Lys Phe Asp Pro Lys Val
                405                 410                 415

Asp Asp Asn Ala Leu Gln Cys Leu Glu Glu Tyr Leu Arg Tyr Lys Ala
                420                 425                 430

Ile Tyr Gly Thr Glu Leu
        435
```

<210> SEQ ID NO 3
<211> LENGTH: 21
<212> TYPE: DNA
<213> ORGANISM: Artificial Sequence
<220> FEATURE:
<223> OTHER INFORMATION: PCR primer TSHC37

<400> SEQUENCE: 3
ggaagttcat acagttccca c                                     21

<210> SEQ ID NO 4
<211> LENGTH: 21
<212> TYPE: DNA
<213> ORGANISM: Artificial Sequence
<220> FEATURE:
<223> OTHER INFORMATION: PCR primer TSHC28

<400> SEQUENCE: 4
cctcccattc aacatcttga g                                     21

<210> SEQ ID NO 5
<211> LENGTH: 31
<212> TYPE: DNA
<213> ORGANISM: Artificial Sequence
<220> FEATURE:
<223> OTHER INFORMATION: PCR primer TSHC45

<400> SEQUENCE: 5
agcgaattca gctcaaagtt cagtcccata g                          31

<210> SEQ ID NO 6
<211> LENGTH: 21
<212> TYPE: DNA
<213> ORGANISM: Artificial Sequence
<220> FEATURE:
<223> OTHER INFORMATION: PCR primer TSHC48

```
<400> SEQUENCE: 6
gtgggaactg tatgaacttc c                                               21

<210> SEQ ID NO 7
<211> LENGTH: 30
<212> TYPE: DNA
<213> ORGANISM: Artificial Sequence
<220> FEATURE:
<223> OTHER INFORMATION: PCR primer TSHC54

<400> SEQUENCE: 7
gcagaattca tggttcaatg gaagagactc                                      30

<210> SEQ ID NO 8
<211> LENGTH: 26
<212> TYPE: DNA
<213> ORGANISM: Artificial Sequence
<220> FEATURE:
<223> OTHER INFORMATION: PCR primer TSHC55

<400> SEQUENCE: 8
cgagaattca ggttgaagtg tgactc                                          26

<210> SEQ ID NO 9
<211> LENGTH: 21
<212> TYPE: DNA
<213> ORGANISM: Artificial Sequence
<220> FEATURE:
<223> OTHER INFORMATION: PCR primer TSHC78

<400> SEQUENCE: 9
gctcggtctc cacctgtctc c                                               21

<210> SEQ ID NO 10
<211> LENGTH: 21
<212> TYPE: DNA
<213> ORGANISM: Artificial Sequence
<220> FEATURE:
<223> OTHER INFORMATION: PCR primer TSHC79

<400> SEQUENCE: 10
ccacaggtag caacgctctc a                                               21

<210> SEQ ID NO 11
<211> LENGTH: 428
<212> TYPE: PRT
<213> ORGANISM: Homo sapiens

<400> SEQUENCE: 11

Met Leu Arg Thr Leu Leu Arg Arg Arg Leu Phe Ser Tyr Pro Thr Lys
1               5                   10                  15

Tyr Tyr Phe Met Val Leu Val Leu Ser Leu Ile Thr Phe Ser Val Leu
            20                  25                  30

Arg Ile His Gln Lys Pro Glu Phe Val Ser Val Arg His Leu Glu Leu
        35                  40                  45

Ala Gly Glu Asn Pro Ser Ser Asp Ile Asn Cys Thr Lys Val Leu Gln
    50                  55                  60

Gly Asp Val Asn Glu Ile Gln Lys Val Lys Leu Glu Ile Leu Thr Val
65                  70                  75                  80

Lys Phe Lys Lys Arg Pro Arg Trp Thr Pro Asp Asp Tyr Ile Asn Met
                85                  90                  95
```

```
Thr Ser Asp Cys Ser Ser Phe Ile Lys Arg Arg Lys Tyr Ile Val Glu
            100                 105                 110

Pro Leu Ser Lys Glu Ala Glu Phe Pro Ile Ala Tyr Ser Ile Val
        115                 120                 125

Val His His Lys Ile Glu Met Leu Asp Arg Leu Leu Arg Ala Ile Tyr
    130                 135                 140

Met Pro Gln Asn Phe Tyr Cys Val His Val Asp Thr Lys Ser Glu Asp
145                 150                 155                 160

Ser Tyr Leu Ala Ala Val Met Gly Ile Ala Ser Cys Phe Ser Asn Val
                165                 170                 175

Phe Val Ala Ser Arg Leu Glu Ser Val Val Tyr Ala Ser Trp Ser Arg
            180                 185                 190

Val Gln Ala Asp Leu Asn Cys Met Lys Asp Leu Tyr Ala Met Ser Ala
        195                 200                 205

Asn Trp Lys Tyr Leu Ile Asn Leu Cys Gly Met Asp Phe Pro Ile Lys
    210                 215                 220

Thr Asn Leu Glu Ile Val Arg Lys Leu Lys Leu Leu Met Gly Glu Asn
225                 230                 235                 240

Asn Leu Glu Thr Glu Arg Met Pro Ser His Lys Glu Glu Arg Trp Lys
                245                 250                 255

Lys Arg Tyr Glu Val Val Asn Gly Lys Leu Thr Asn Thr Gly Thr Val
            260                 265                 270

Lys Met Leu Pro Pro Leu Glu Thr Pro Leu Phe Ser Gly Ser Ala Tyr
        275                 280                 285

Phe Val Val Ser Arg Glu Tyr Val Gly Tyr Val Leu Gln Asn Glu Lys
    290                 295                 300

Ile Gln Lys Leu Met Glu Trp Ala Gln Asp Thr Tyr Ser Pro Asp Glu
305                 310                 315                 320

Tyr Leu Trp Ala Thr Ile Gln Arg Ile Pro Glu Val Pro Gly Ser Leu
                325                 330                 335

Pro Ala Ser His Lys Tyr Asp Leu Ser Asp Met Gln Ala Val Ala Arg
            340                 345                 350

Phe Val Lys Trp Gln Tyr Phe Glu Gly Asp Val Ser Lys Gly Ala Pro
        355                 360                 365

Tyr Pro Pro Cys Asp Gly Val His Val Arg Ser Val Cys Ile Phe Gly
    370                 375                 380

Ala Gly Asp Leu Asn Trp Met Leu Arg Lys His His Leu Phe Ala Asn
385                 390                 395                 400

Lys Phe Asp Val Asp Val Asp Leu Phe Ala Ile Gln Cys Leu Asp Glu
                405                 410                 415

His Leu Arg His Lys Ala Leu Glu Thr Leu Lys His
            420                 425

<210> SEQ ID NO 12
<211> LENGTH: 400
<212> TYPE: PRT
<213> ORGANISM: Homo sapiens

<400> SEQUENCE: 12

Met Pro Leu Ser Met Arg Tyr Leu Phe Ile Ile Ser Val Ser Ser Val
1               5                   10                  15

Ile Ile Phe Ile Val Phe Ser Val Phe Asn Phe Gly Gly Asp Pro Ser
            20                  25                  30

Phe Gln Arg Leu Asn Ile Ser Asp Pro Leu Arg Leu Thr Gln Val Cys
        35                  40                  45
```

-continued

```
Thr Ser Phe Ile Asn Gly Lys Thr Arg Phe Leu Trp Lys Asn Lys Leu
    50                  55                  60
Met Ile His Glu Lys Ser Ser Cys Lys Glu Tyr Leu Thr Gln Ser His
65                  70                  75                  80
Tyr Ile Thr Ala Pro Leu Ser Lys Glu Glu Ala Asp Phe Pro Leu Ala
                85                  90                  95
Tyr Ile Met Val Ile His His His Phe Asp Thr Phe Ala Arg Leu Phe
            100                 105                 110
Arg Ala Ile Tyr Met Pro Gln Asn Ile Tyr Cys Val His Val Asp Glu
            115                 120                 125
Lys Ala Thr Thr Glu Phe Lys Asp Ala Val Glu Gln Leu Leu Ser Cys
            130                 135                 140
Phe Pro Asn Ala Phe Leu Ala Ser Lys Met Glu Pro Val Val Tyr Gly
145                 150                 155                 160
Gly Ile Ser Arg Leu Gln Ala Asp Leu Asn Cys Ile Arg Asp Leu Ser
                165                 170                 175
Ala Phe Glu Val Ser Trp Lys Tyr Val Ile Asn Thr Cys Gly Gln Asp
            180                 185                 190
Phe Pro Leu Lys Thr Asn Lys Glu Leu Val Gln Tyr Leu Lys Gly Phe
            195                 200                 205
Lys Gly Lys Asn Ile Thr Pro Gly Val Leu Pro Pro Ala His Ala Ile
210                 215                 220
Gly Arg Thr Lys Tyr Val His Gln Glu His Leu Gly Lys Glu Leu Ser
225                 230                 235                 240
Tyr Val Ile Arg Thr Thr Ala Leu Lys Pro Pro Pro His Asn Leu
                245                 250                 255
Thr Ile Tyr Phe Gly Ser Ala Tyr Val Ala Leu Ser Arg Glu Phe Ala
            260                 265                 270
Asn Phe Val Leu His Asp Pro Arg Ala Val Asp Leu Leu Gln Trp Ser
            275                 280                 285
Lys Asp Thr Phe Ser Pro Asp Glu His Phe Trp Val Thr Leu Asn Arg
    290                 295                 300
Ile Pro Gly Val Pro Gly Ser Met Pro Asn Ala Ser Trp Thr Gly Asn
305                 310                 315                 320
Leu Arg Ala Ile Lys Trp Ser Asp Met Glu Asp Arg His Gly Gly Cys
                325                 330                 335
His Gly His Tyr Val His Gly Ile Cys Ile Tyr Gly Asn Gly Asp Leu
            340                 345                 350
Lys Trp Leu Val Asn Ser Pro Ser Leu Phe Ala Asn Lys Phe Glu Leu
            355                 360                 365
Asn Thr Tyr Pro Leu Thr Val Glu Cys Leu Glu Leu Arg His Arg Glu
    370                 375                 380
Arg Thr Leu Asn Gln Ser Glu Thr Ala Ile Gln Pro Ser Trp Tyr Phe
385                 390                 395                 400
```